US010083365B2

(12) United States Patent
Schiller et al.

(10) Patent No.: US 10,083,365 B2
(45) Date of Patent: Sep. 25, 2018

(54) OPTICAL READING OF EXTERNAL SEGMENTED DISPLAY

(71) Applicant: VALIDIC, INC., Durham, NC (US)

(72) Inventors: Andrew Schiller, Chapel Hill, NC (US); Eric Reifsnider, Chapel Hill, NC (US); Stanley J Smith, Bradenton, FL (US); William Matthew Jones, Raleigh, NC (US); Marc Christopher Sebes, Cary, NC (US); Ameir Ali Khaled Al-Zoubi, Apex, NC (US); Stephen Jacob Dycus, Raleigh, NC (US)

(73) Assignee: VALIDIC, Durham, NC (US)

( * ) Notice: Subject to any disclaimer, the term of this patent is extended or adjusted under 35 U.S.C. 154(b) by 0 days.

(21) Appl. No.: 15/220,612

(22) Filed: Jul. 27, 2016

(65) Prior Publication Data
US 2017/0193322 A1    Jul. 6, 2017

Related U.S. Application Data

(60) Provisional application No. 62/274,665, filed on Jan. 4, 2016.

(51) Int. Cl.
| | | |
|---|---|---|
| *G06K 9/34* | (2006.01) | |
| *A61B 5/00* | (2006.01) | |
| *G06K 9/32* | (2006.01) | |
| *G06K 9/62* | (2006.01) | |
| *G06T 7/00* | (2017.01) | |

(Continued)

(52) U.S. Cl.
CPC ............ *G06K 9/344* (2013.01); *A61B 5/0077* (2013.01); *A61B 5/72* (2013.01); *A61B 5/742* (2013.01); *G06K 9/00* (2013.01); *G06K 9/3208* (2013.01); *G06K 9/6201* (2013.01); *G06T 7/0012* (2013.01); *G06K 9/78* (2013.01); *G06K 2209/01* (2013.01); *G06K 2209/03* (2013.01); *G06T 2207/30004* (2013.01)

(58) Field of Classification Search
CPC combination set(s) only.
See application file for complete search history.

(56) References Cited

U.S. PATENT DOCUMENTS

| | | |
|---|---|---|
| 8,015,600 B2 | 9/2011 | Sinn et al. |
| 8,442,835 B2 | 5/2013 | Ji et al. |
| 8,510,133 B2 | 8/2013 | Peak et al. |

(Continued)

FOREIGN PATENT DOCUMENTS

| | | |
|---|---|---|
| WO | WO 2011/028261 A2 | 3/2011 |
| WO | WO 2014/058802 A1 | 4/2014 |

(Continued)

OTHER PUBLICATIONS

Wolf et al.; "Methods, Devices, and Systems to Empower Meaningful Use of After-Visit Systems"; U.S. Appl. No. 61/933,768, filed Jan. 30, 2014.

(Continued)

*Primary Examiner* — Tsung-Yin Tsai
(74) *Attorney, Agent, or Firm* — CARR Law Firm PLLC

(57) ABSTRACT

The present invention includes a method for optical character recognition of external segmented displays using a camera connected to a reading device and a data reading application on the reading device.

40 Claims, 21 Drawing Sheets

(51) Int. Cl.
*G06K 9/00* (2006.01)
*G06K 9/78* (2006.01)

(56) References Cited

U.S. PATENT DOCUMENTS

| | | | |
|---|---|---|---|
| 8,534,549 | B2 | 9/2013 | Sarkis, Jr. et al. |
| 8,590,027 | B2 | 11/2013 | Rowley |
| 8,610,769 | B2 * | 12/2013 | Buxton ................ H04N 7/183 348/121 |
| 8,666,768 | B2 | 3/2014 | Ji et al. |
| 8,679,014 | B2 | 3/2014 | Bennett et al. |
| 8,737,971 | B2 | 5/2014 | van Rooyen et al. |
| 9,351,641 | B2 | 5/2016 | Neff |
| 9,754,370 | B2 | 9/2017 | Neff |
| 2006/0005237 | A1 | 1/2006 | Kobata et al. |
| 2006/0089542 | A1 | 4/2006 | Sands |
| 2006/0247505 | A1 | 11/2006 | Siddiqui |
| 2007/0035403 | A1 | 2/2007 | Krishna et al. |
| 2008/0301444 | A1 | 12/2008 | Kim et al. |
| 2009/0192813 | A1 * | 7/2009 | Gejdos ................ G16H 10/65 |
| 2010/0222648 | A1 | 9/2010 | Tan |
| 2010/0228676 | A1 * | 9/2010 | Librizzi ................ G06Q 10/00 705/306 |
| 2010/0249541 | A1 | 9/2010 | Geva |
| 2011/0082711 | A1 | 4/2011 | Poeze et al. |
| 2011/0144451 | A1 | 6/2011 | Robertson |
| 2011/0161100 | A1 | 6/2011 | Peak et al. |
| 2011/0166628 | A1 | 7/2011 | Jain |
| 2011/0190581 | A1 | 8/2011 | Bennett |
| 2011/0221595 | A1 | 9/2011 | Koraichi et al. |
| 2012/0070090 | A1 * | 3/2012 | Chang ................ G06K 9/00 382/218 |
| 2012/0165617 | A1 | 6/2012 | Vesto et al. |
| 2012/0182939 | A1 | 7/2012 | Rajan et al. |
| 2012/0191562 | A1 * | 7/2012 | Bowles ................ G06Q 10/00 705/26.3 |
| 2012/0218123 | A1 | 8/2012 | Ji et al. |
| 2012/0220835 | A1 | 8/2012 | Chung et al. |
| 2012/0265029 | A1 | 10/2012 | Fahey |
| 2013/0019295 | A1 | 1/2013 | Park et al. |
| 2013/0097686 | A1 | 4/2013 | Towata |
| 2013/0127980 | A1 * | 5/2013 | Haddick ................ G06F 3/013 348/14.08 |
| 2013/0155474 | A1 * | 6/2013 | Roach ................ G06Q 20/322 358/505 |
| 2013/0162160 | A1 | 6/2013 | Ganton et al. |
| 2013/0166332 | A1 * | 6/2013 | Hammad ................ G06Q 40/10 705/5 |
| 2013/0198144 | A1 * | 8/2013 | Bowles ................ G06Q 10/30 707/668 |
| 2013/0198834 | A1 | 8/2013 | Kirsch |
| 2013/0311318 | A1 * | 11/2013 | Librizzi ................ G06Q 10/00 705/26.3 |
| 2013/0346089 | A1 | 12/2013 | Margon |
| 2014/0003577 | A1 | 1/2014 | Ferro |
| 2014/0012511 | A1 | 1/2014 | Mensinger et al. |
| 2014/0012544 | A1 | 1/2014 | Mensinger et al. |
| 2014/0040993 | A1 | 2/2014 | Lorenzo et al. |
| 2014/0067426 | A1 | 3/2014 | Neff |
| 2014/0100879 | A1 | 4/2014 | Kharebov et al. |
| 2014/0139616 | A1 * | 5/2014 | Pinter ................ A61B 5/0008 348/14.08 |
| 2015/0213194 | A1 | 7/2015 | Wolf et al. |
| 2015/0365412 | A1 | 12/2015 | Innes et al. |
| 2015/0381621 | A1 | 12/2015 | Innes et al. |
| 2016/0098689 | A1 * | 4/2016 | Bowles ................ G06Q 20/18 705/23 |
| 2016/0098690 | A1 * | 4/2016 | Silva ................ G06Q 10/30 705/21 |
| 2016/0127343 | A1 | 5/2016 | Schiller et al. |
| 2016/0320889 | A1 * | 11/2016 | Jenkinson ............ G06F 3/0418 |
| 2016/0353030 | A1 * | 12/2016 | Gao ................ H04N 5/23293 |
| 2018/0115555 | A1 | 4/2018 | Schiller et al. |

FOREIGN PATENT DOCUMENTS

| | | |
|---|---|---|
| WO | WO 2014/095644 | 6/2014 |
| WO | WO 2016/073795 A1 | 5/2016 |
| WO | WO 2017/120223 A1 | 7/2017 |

OTHER PUBLICATIONS

PCT/US2017/012175; International Search Report and Written Opinion; Mar. 30, 2017.

Maienbourn et al; "Semantics an International Handbook of Natural Language Meaning"; Jan. 1, 2011, De Gruyter Mouton, XP055357650, p. 1485.

Doermann et al; "Handbook of Document Image Processing and Recognition"; Jan. 1, 2014; Springer, XP055357826, pp. 844-833.

Lu, Tong et al; "Video Text Detection"; Jan. 1, 2014; Springer, XP055357831, pp. 14-16.

Kulkarni, Prach H et al; "IoT based data processing for automated industrial meter reader using Raspberry Pi"; 2016 IOTA, IEEE, Jan. 11, 2016, pp. 107-111; XP032958403; abstract p. 108, para 1, fig. 1-5.

De Lima, Danilo Alves et al: "A Computer Vision System to read Meter Displays"; 16th IMEKO TC4 Symposium Exploring New Frontiers of Instrumentation and Methods for Electrical and Electronic Measurements; Aug. 22, 2008; XP055357836.

Chen, Kuo-Yi et al; "A low-cost universal reader for digital displays of medical monitors"; 2010 2nd International Conference on Mechanical and Electronics Engineering (ICMEE 2010}: Kyoto, Japan; Aug. 1, 2010; pp. V2-79-83.

CardioNet; Overview—Mobile Cardiac Outpatient Telemetry; 2012; https://www.cardionet.com/.

Chung, et al.; A cell phone based health monitoring system with self analysis processor using wireless sensor network technology; ConfProc IEEE Eng Med Biol Soc. 2007;2007; pp. 3705-3708.

eCaring; The heart of better care management; 2013; http://ecaring.com/.

Glooko; Mobile diabetes management; 2013; https://www.glooko.com/.

Healthsense; eNeighbor remote monitoring system; 2012; http://healthsense.com/index. php/products/remote-monitoring/eneighbor.

Healthvault; Health information online; 2013 Microsoft; https://www.healthvault.com/us/en.

IBGStar; Blood glucose meter; 2013; http://www.ibgstar.us/.

Intuitivehealth; Healthcare information website; 2010; http://www.intuitivehealth.com/.

MedApps; HealthAIR remote health monitoring device; 2011; http://www.medapps.net/healthair.html.

Myfitnesscompanion; Take control of your life; 2013; http://myfitnesscompanion.com/.

QualcommLife; Mobilizing healthcare; 2012; http://www.qualcommlife.com/.

ScienceDaily; Monitoring Your Health With Your Mobile Phone; Oct. 11, 2010;.

Sinovo; We care for you; Information and website; 2013; http://www.sidiary.org/.

Visimobile; Overview—ViSi Mobile system; 2013; http://www.visimobile.com/.

PCT/US2013/063733; International search report and written opinion; dated Mar. 11, 2014.

Network Working Group; Request for Comments No. 2616, Hypertext Transfer Protocol—HTTP/1.1; Jun. 1999.

Internet Engineering Task Force (IETF); Request for Comments No. 5849, the OAuth 1.0 Protocol; Apr. 2010.

Internet Engineering Task Force (IETF); Request for Comments No. 6749, the OAuth 2.0 Authorization Framework; Oct. 2012.

Google Developers; Using OAuth 2.0 for Devices; Aug. 18, 2014;.

Kharebov et al.; U.S. Appl. No. 61/711,141, filed Oct. 8, 2012, entitled "Systems and Methods for Device and Meter Monitoring".

Kharebov et al.; U.S. Appl. No. 14/047,751, filed Oct. 7, 2013, entitled "Systems and Methods for Device and Meter Monitoring".

(56) References Cited

OTHER PUBLICATIONS

PCT/US2015/059343; International Search Report and Written Opinion, by the ISA/US; dated Mar. 2, 2016.
Dowling et al; A proxy-based security architecture for Internet applications in an extranet environment; 107-118; 2001; [retrieved on Dec. 21, 2015]; retrieved from http://xa.yimg.com/kq/groups/13354653/656473622/name/sajjad.pdf.

* cited by examiner

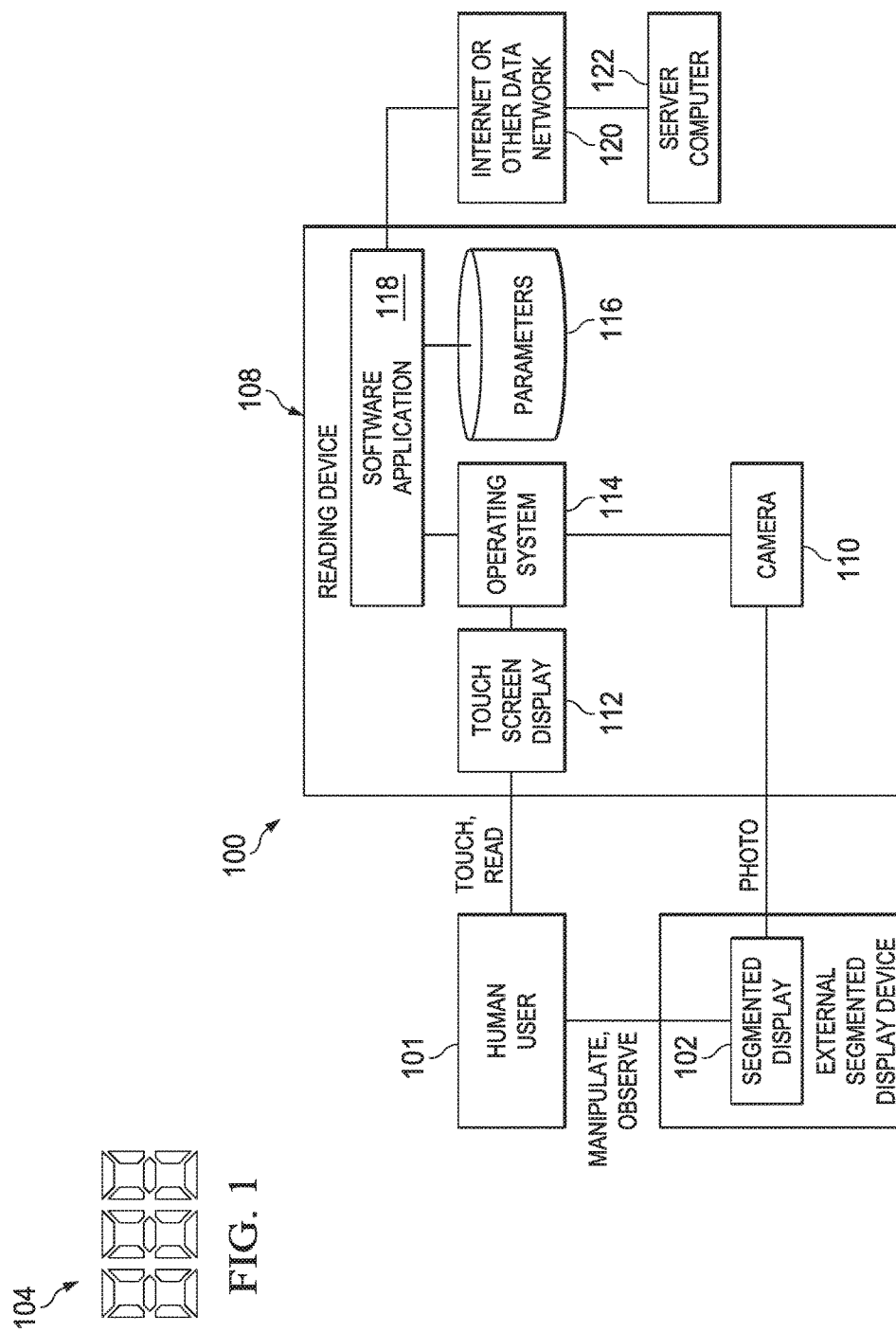

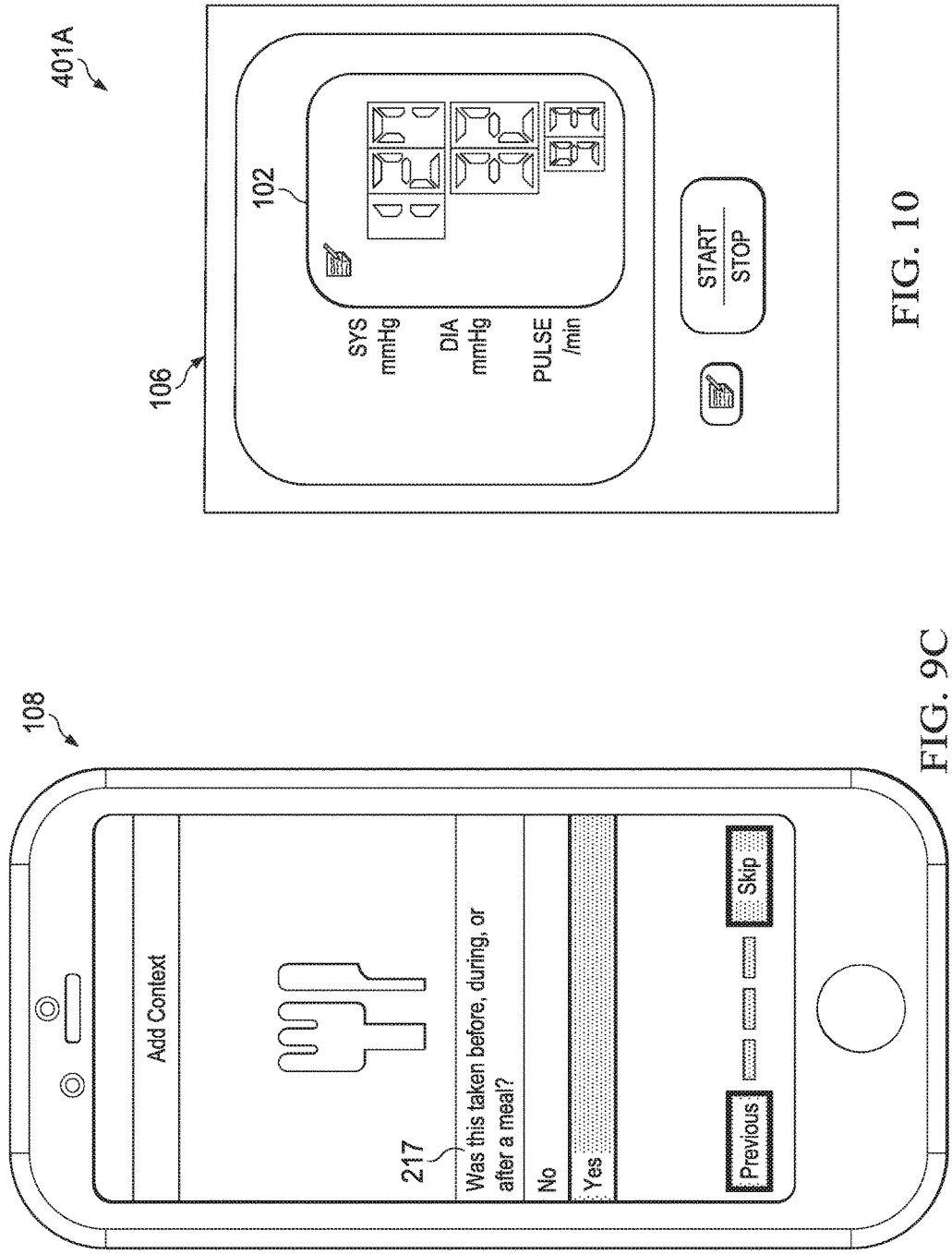

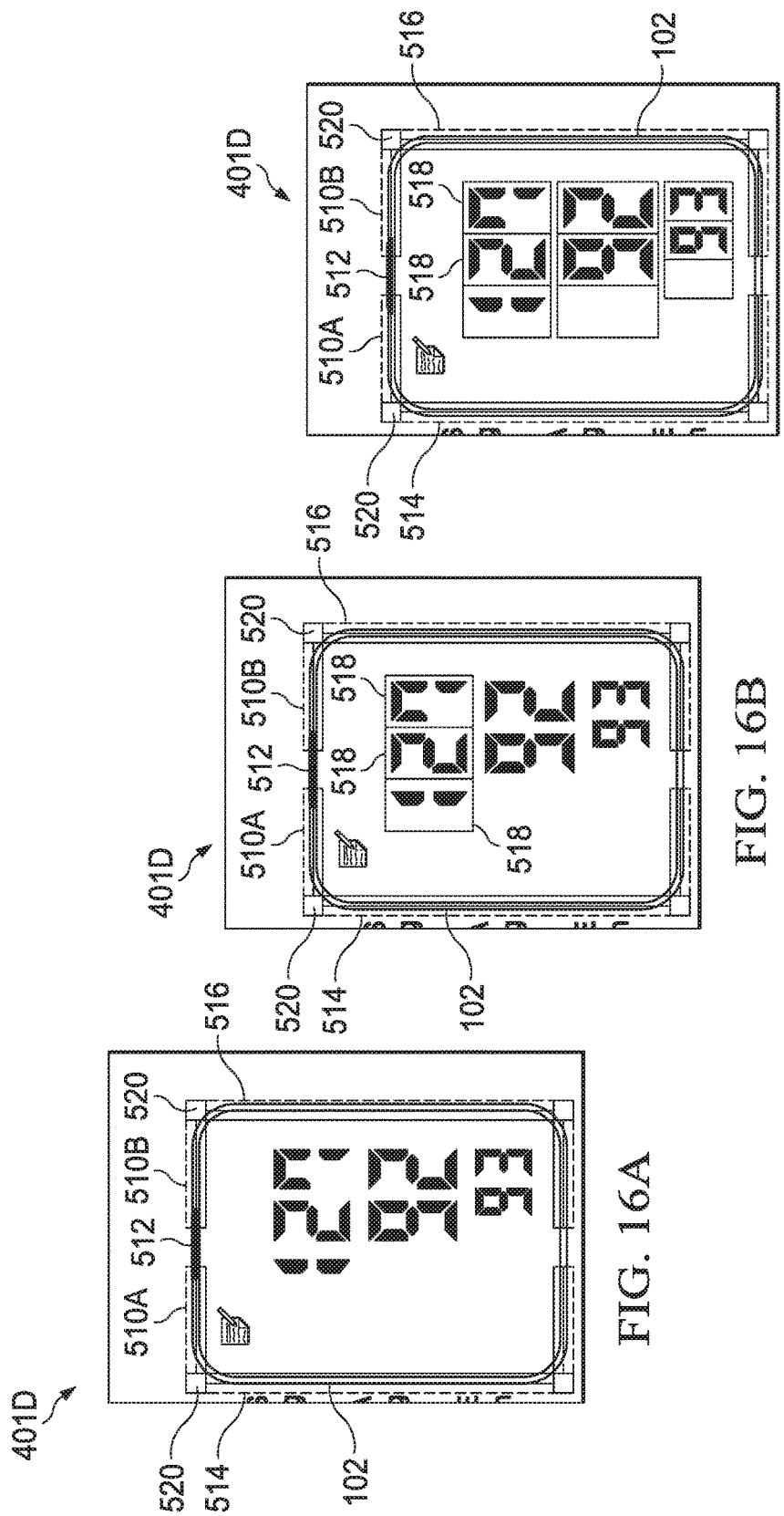

OPTICAL READING OF EXTERNAL SEGMENTED DISPLAY

CROSS-REFERENCE TO RELATED APPLICATIONS

The application relates to, and claims the benefit of the filing date of, co-pending U.S. provisional patent application Ser. No. 62/274,665 entitled "OPTICAL READING OF EXTERNAL SEGMENTED DISPLAY," filed Jan. 4, 2016, the entire contents of which are incorporated herein by reference for all purposes.

TECHNICAL FIELD

This application relates to optical character recognition (OCR) and, more particularly, to OCR of external displays.

BACKGROUND

Computer devices, such as desktop computers, laptop computers, smartphones, and tablets, are commonly used to record health data. For example, a smartphone application may track a user's blood glucose, blood pressure, and weight over time. However, the smartphone alone may be unable to measure the health data. A user may use medical devices external to the smartphone to measure the health data. Examples of external medical devices include personal glucose meters, blood pressure meters, weight scales, other biometric meters, and the like.

In many cases, an external medical device cannot electronically communicate its health data measurements to a computer reading device. The medical device may be designed only to output its measurements on a built-in display. With such a medical device, the user conventionally reads the display and manually enters the measurements into the computer reading device application. This approach is time-consuming and susceptible to user error.

It would be desirable if a computer device could obtain measurements from an external medical device without relying solely on manual entry by a user or on electronic communication from the external device to the computer device.

SUMMARY

Provided is a method for optical character recognition (OCR) of external displays.

BRIEF DESCRIPTION OF DRAWINGS

Reference is now made to the following Detailed Description taken in conjunction with the accompanying drawings, in which:

FIG. 1 is an idealized display of an exemplary seven-segment display device;

FIG. 2 is a system architecture diagram for an exemplary system for optically reading an external segmented display;

FIGS. 9A-9C depicts metadata survey screens of an exemplary application for optically reading an external segmented display;

FIG. 10 depicts an exemplary LCD/LED device front panel, including the display;

FIGS. 16A-16C depict exemplary digit cell reckoning operations;

DETAILED DESCRIPTION OF THE INVENTION

Figure 3:
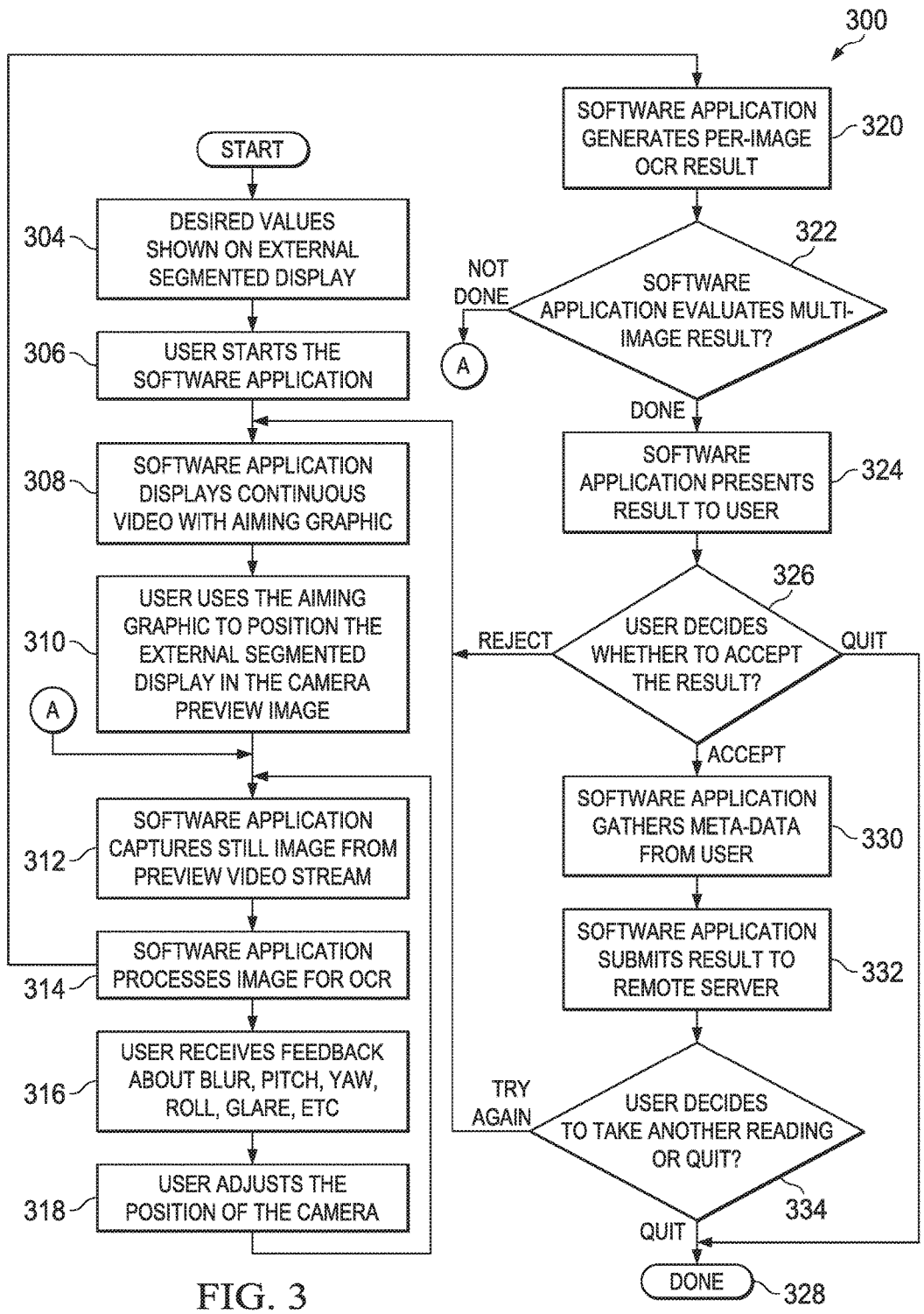
FIG. 3 is a flow diagram of the overall flow of an exemplary system for optically reading an external segmented display.

In the following discussion, numerous specific details are set forth to provide a thorough explanation. However, such specific details are not essential. In other instances, well-known elements have been illustrated in schematic or block diagram form. Additionally, for the most part, specific details within the understanding of persons of ordinary skill in the relevant art have been omitted. Furthermore, health data and seven-segment displays will be discussed as examples, but the following discussion is not limited to health data or seven-segment displays.

Using a camera, a computer reading device may optically read an external segmented display. The external segmented display may be on an external device. The external device may have no wired data connections and no wireless data connections to the computer reading device.

The external segmented display may be an LCD display or an LED display. The display may also be any other segmented display, but for ease of discussion the display will be referred to as if it were an LCD display or an LED display. The external segmented display may be seven-segment, fourteen-segment, or sixteen-segment. The external segmented display may also have another number of segments. Referring to FIG. 1, depicted is an exemplary idealized seven-segment display 104.

The external segmented display may be part of a lightweight portable medical device such as a personal glucose meter, blood pressure meter, weight scale, or other biometric meter. The external segmented display may also be part of a fixed device, such as a clinical desktop biometric meter. One skilled in the art may easily adapt this disclosure to work with a wide variety of segmented displays built into a variety of measurement devices.

Referring to FIG. 2, depicted is a system architecture diagram showing an exemplary system 100 comprising a human user 101, an external segmented display device 106, and a reading device 108. The external segmented display device 106 may further comprise a segmented display 102. The reading device 108 may further comprise a camera 110, a touch screen display 112, an operating system 114, one or more configuration parameters 116, a software application 118, a data network 120, and a server computer 122.

The system 100 may be an interactive system of software and hardware, incorporating real time user feedback at multiple stages of information processing. The reading device 108 may run the operating system 114. The operating system 114 may be a general operating system.

The reading device 108 may be connected to the camera 110. The camera 110 may be built-in or external. The camera 110 may be capable of recording "live" video preview (at least sixteen frames per second). The reading device 1080 may be capable of displaying the "live" vide preview recorded by the camera 110. The reading device 108 may be a smartphone running the Apple iOS operating system, but other reading devices and operating systems may be used. For example, the reading device 108 may be a tablet and the operating system 114 may be the Android operating system.

The reading device 108 and the operating system 114 may host the software application 118. The software application 118 may control the camera 110, provide a video preview to the user 101, and interact with the user 101 to display graphical and textual prompts in real time. When the software application 118 finishes processing the reading of the external segmented display 102, the software application 118 may display a result to the user 101, provide a means for uploading the result to other computer systems via online connectivity, and allow the user 101 to proceed with another reading.

The software application 118 may be an Apple iOS application. The reading device 108 may be an Apple iPhone 5S or another Apple iPhone model. One skilled in the art could, on a variety of operating systems, create a variety of applications that use similar displays and processing techniques, either as standalone applications or as part of other more general applications.

The application 118 may have one or more configuration parameters 116 that adjust the behavior of the application 116 depending on the external segmented display device 106 that is being read. The parameters 116 may be mostly empirically derived, but some may be analytically calculated. A given set of configuration parameters 116 may apply to a given set of external display devices to be read. Possible specific parameters will be discussed below.

A user 101 may cause the reading device 108 to read an external segmented display 102 by using the software application 118 and physically manipulating the external device 106 containing the display 102.

Figure 4A:
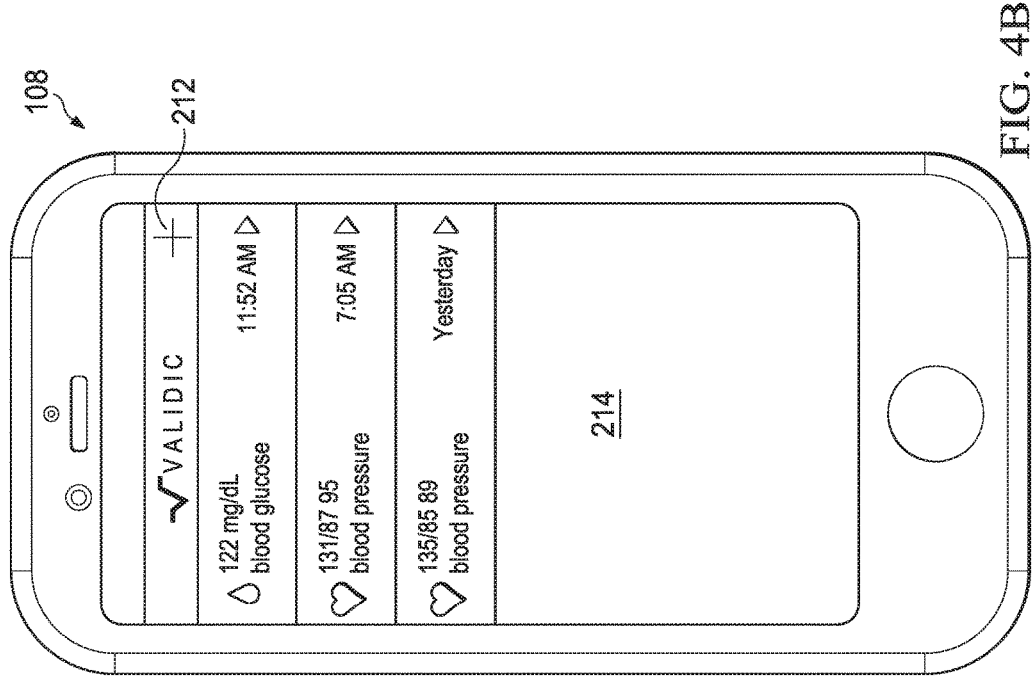
FIG. 4A is a configuration screen of an exemplary application for optically reading an external segmented display.

Referring to FIG. 4A, depicted is a configuration screen 200 of an exemplary software application 118 on a reading device 108. This configuration screen 200 may be the initial user interface of the software application 118. The configuration screen 200 may provide a selector for changing the model of external device 106 to be read, along with a user interface button for initiating a reading session 302.

A "reading session" 302 may be defined as one cycle of using the software application 118 to read the segmented display 102 of the external segmented display device 106, generating a final result string 216. The software application 118 may be reused in that the user 101 may perform serial reading sessions with one or more external devices to get successive readings. Referring to FIG. 3, depicted is a flow diagram for an exemplary overall optical reading system 300. A reading session 302 may begin at step 308 and end at step 326.

Figure 4B:
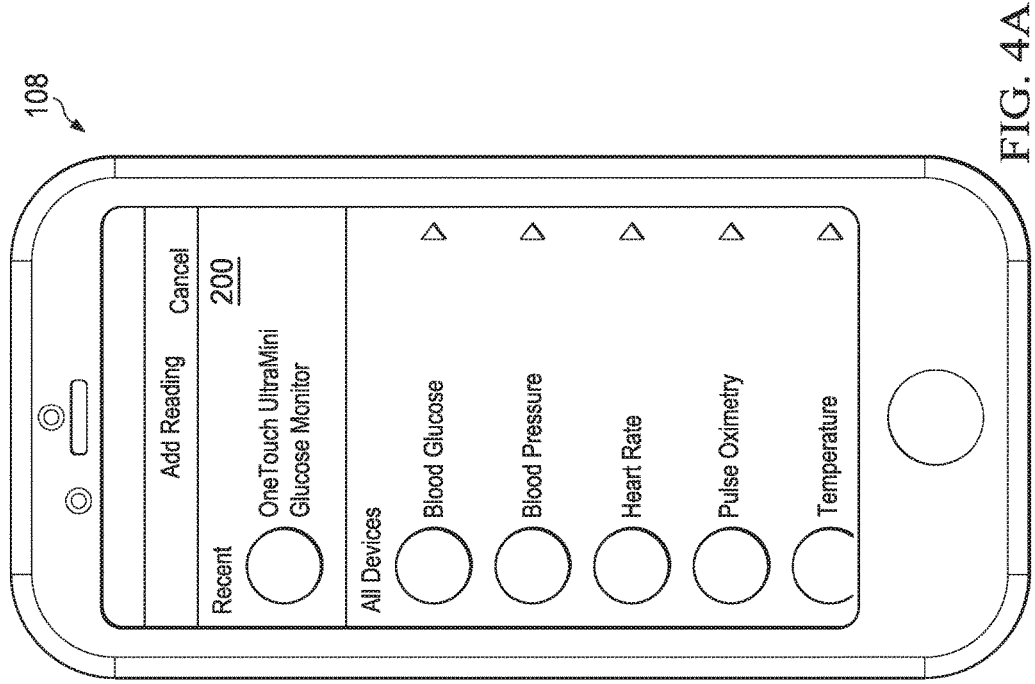
FIG. 4B is a recent results screen of an exemplary application for optically reading an external segmented display.

Referring to FIG. 4B, the software application 118 may show the user 101 a display of the most recent OCR results. The result the software application 118 has just most recently gathered may be shown at the top of the display. The recent results screen 214 may have a button, such as the "+" button 212 in FIG. 4B, to start a new reading session 302. Upon pressing the button 212, the user 101 may be taken to the configuration screen 200 like that of FIG. 4A.

Figure 5:
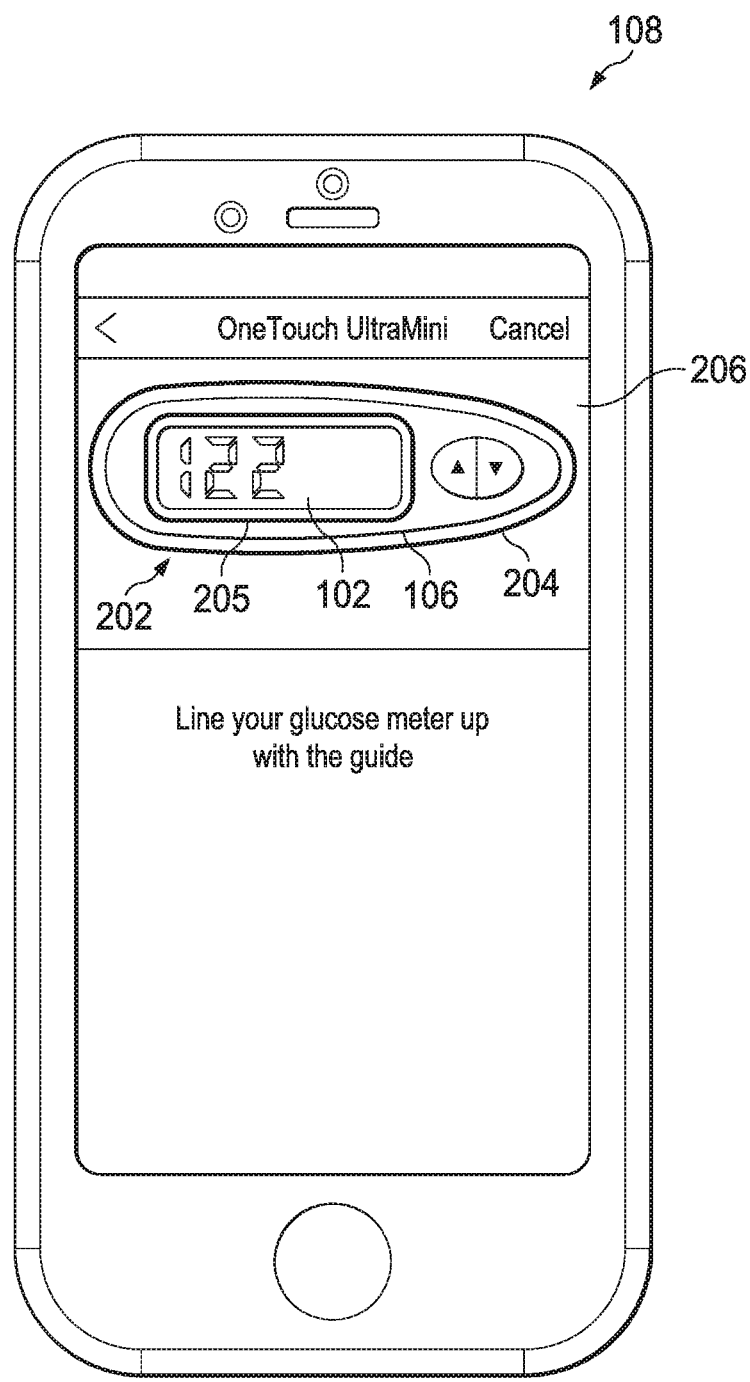
FIG. 5 is a video preview screen of an exemplary application for optically reading an external segmented display.

Referring to FIG. 5, depicted is a video preview screen 202 for an exemplary reading session 302. The video preview screen 202 may be the main user interface of the software application 118. The reading device 108 may view the segmented display 102 using the camera 110 to show on the video preview screen 202 a video preview 206 of the segmented display 102.

The resolution of the video preview 206 may be set to the default resolution for the device 108 or a minimum resolution, whichever is greater. For smartphone reading devices, this typically results in use of the default video preview resolution, which is optimized by the operating system 114. The minimum resolution may be relatively low by modern smartphone standards. For example, a minimum resolution of 640 pixels wide by 480 pixels tall may be sufficient.

The reading device 108 may continuously display the video preview 206 from the camera 110 in order to allow the user 101 to aim with a graphical aiming cue 204. The graphical aiming cue 204 may be a simple aiming rectangle. Other and more complex aiming figures may be used as graphical aiming cues. Examples include ovals, rectangles, squares, quadrilaterals, and the like, as well as shapes representing more or less detailed representations of the device's front panel (including the segmented display panel along with other elements on the face of the device), etc. However, a simple aiming rectangle may be a sufficient graphical aiming cue 204. In FIGS. 6A-6H, 8A, and 8B, the graphical aiming cue 204 is shown as a darkened outline superimposed over the face of the external device 106 with a second darkened outline 205 superimposed over the segmented display 102 of the external device 106.

When the user 101 chooses to begin a reading session 302 the video preview 206 may be viewed on the reading device 108. The graphical aiming cue 204 may be superimposed over the video preview 206. The user 101 may be instructed to position the graphical aiming cue 204 such that it matches up with specific visible features of the external device 106. Where the graphical aiming cue 204 is a simple rectangle, the user 101 may be instructed to aim the rectangle so that it tightly encloses the segmented display 102 portion of the overall external device front panel. The user 101 may be instructed to use real time feedback from the live video preview 206 to adjust the aim.

While the live video preview 206 is displayed continuously to the user 101, with the graphical aiming cue 204 superimposed on the display screen of the reading device 108, the software application 118 may capture one or more sample individual frames from the live video preview 206 for analysis. The sampling of the one or more still images from the live video preview 206 may be performed at the highest rate supported by the reading device 108 and the operating system 114, but no higher than the rate at which the one or more images may be processed by the image processing stages described below, with reference to FIG. 7.

Each of the one or more still images may be submitted to the image processing stages described below, and processed by an image processing subsystem 400 (shown in FIG. 7), while the live video preview 206 is ongoing. Using this background processing approach for analyzing the one or more still images may ensure that the user 101 does not need to explicitly interact with the software application 118 to take a picture, such as pressing a shutter button. Instead, the user 101 may simply concentrate on aiming the camera 110 and on interpreting the live graphical user feedback cues, described below, provided by the software application 118. The background processing may also comprise a parallel processing approach. In an embodiment, the image processing subsystem 400 is able to process at least four images per second. In another embodiment, the image processing system 400 is able to process at least eight images per second. In another embodiment, the image processing system 400 is typically able to process sixteen images per second.

The one or more sampled still images may be processed as detailed below, and an OCR partial result 208 of reading the external device 106 may be generated for each of the sampled images, along with user feedback cues 210 to enable the user 101 to help adjust the system in real time to achieve a better result. An individual image may be used to develop the OCR partial result 208. The OCR final result string 216 may take into account the OCR partial results 208 from multiple images, as will be described below.

Referring to FIGS. 6A-6H, depicted are examples of real time graphical feedback cues 210 that prompt the user 101 to adjust the camera 110. In addition to showing the graphical aiming cue 204 superimposed over the live video preview 206, the user interface of the software application 118 may display these real time feedback cues 210. The real time graphical cues 210 may be triggered by output from analysis of the one or more individual captured images, and may be displayed as a result of individual image processing by the image processing subsystem 400.

The real time feedback cues 210 that may be generated by analysis of an image will be described below in connection with individual image processing steps. Some real time feedback cues 210 may be prompts for the user 101 to adjust the camera 110 or the external segmented display device 106. Broadly speaking, these prompts may include glare indication 210A (directing the user 101 to tilt the external device 106 or change the lighting to remove glare from the external device front panel), rotation (yaw) detection (directing the user 101 to adjust the angle of the camera 110 to straighten the image in real time), pitch/roll detection (also directing the user 101 to adjust the angle of the camera 110), image size problems (directing the user 101 to move the camera 110 closer or farther away). The real time feedback cues 210G may also notify the user 101 of the OCR partial result 208 from the most recent image, for example a number or part of a reading. The user 101 may assess the OCR partial result 208 to get an indication of the status and process of the software application 118 in getting a reading, and to get an indication of which camera angles and lighting scenarios work better or worse.

The real time feedback cues 210 may provide feedback to the user 101 during the live video preview 206. The user feedback cues 210 may be triggered by analysis of individual images. However, individual images are typically processed multiple times per second. A typical smartphone may process at least ten images per second. As a result, the real time feedback cues 210 may be shown for a duration greater than one individual analysis cycle, in order for the user 101 to recognize the cues 210 and act upon them. In an embodiment, real time feedback cues 210 are shown on the screen for a minimum of one-half of one second.

Figure 6B:
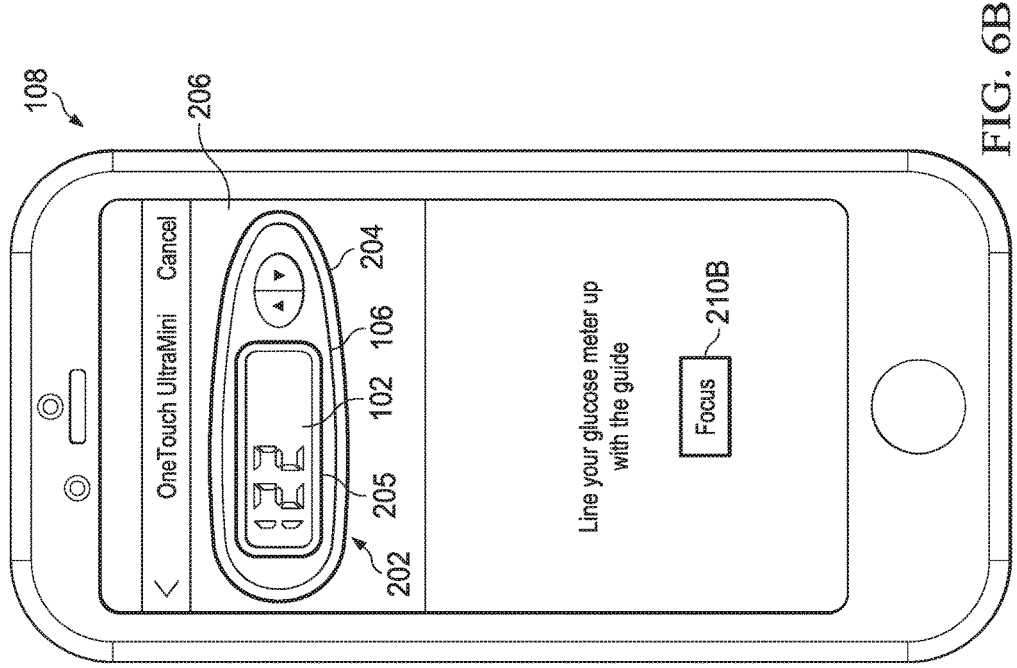
FIGS. 6A-6H depict user feedback indications for the video preview screen of FIG. 5.
Figure 6A:
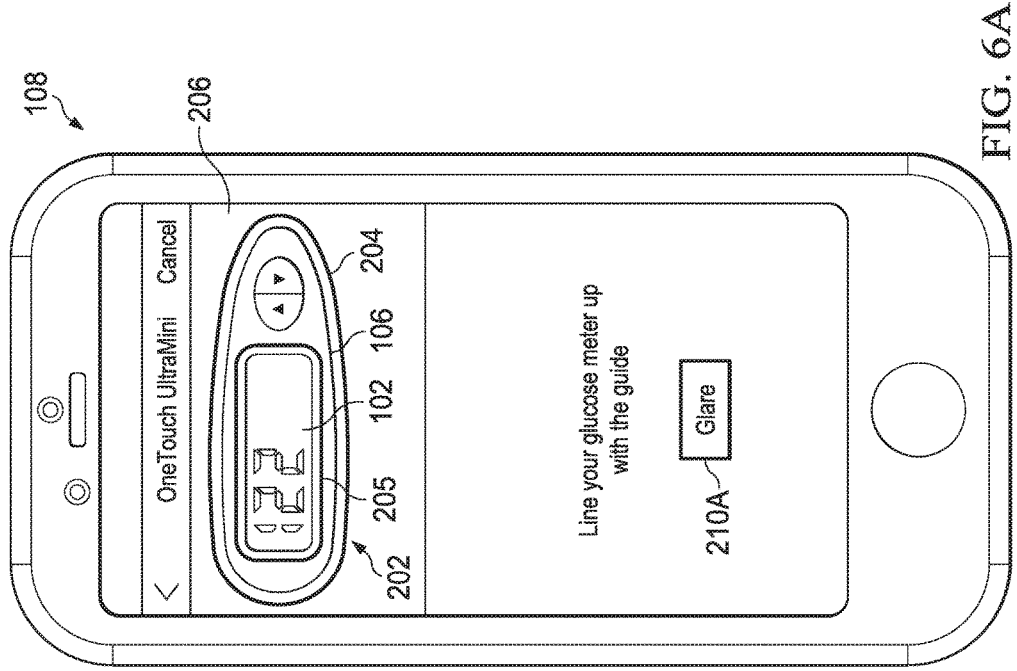
Figure 6D:
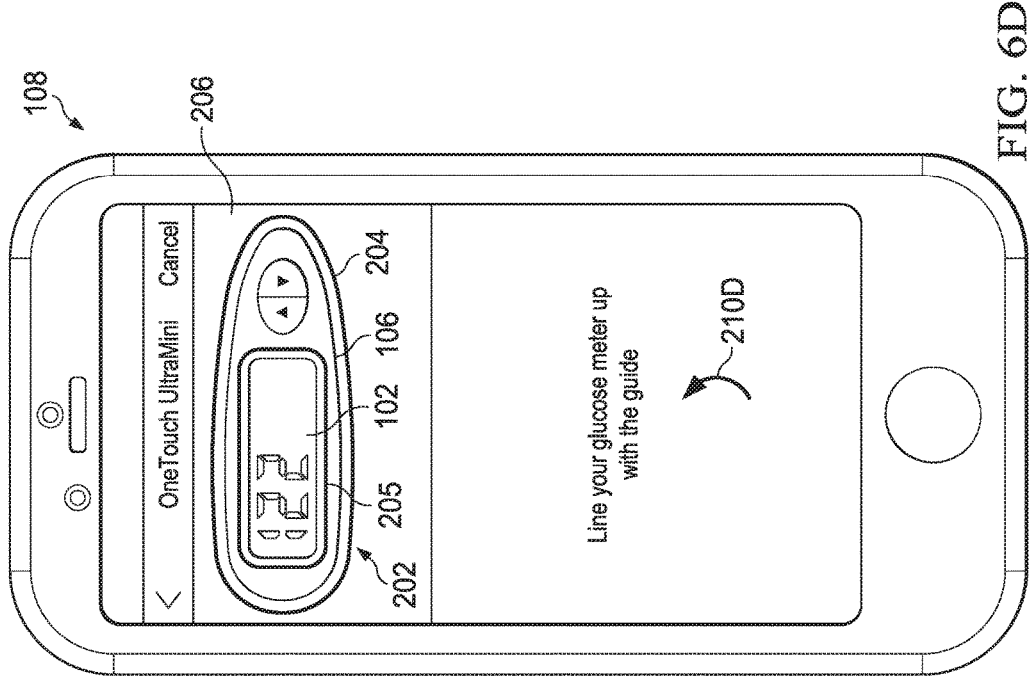

Many hardware devices, particularly smartphones, offer live accelerometer input. During the live video preview 206, the software application 118 may employ the live accelerometer input to detect whether the user 101 is responding to prompts that should lead to a change in the angle of the camera 110. As shown in FIG. 6H, if the user 101 is not complying with the prompts, an instructional message 210H may be shown after the current reading session 302 is complete. The instructional message 210H may help the user 101 understand how to use the provided live feedback cues 210.

The correctness and timeliness of the response by the user 101 to feedback cues 210 to zoom, pan, or tilt may be used by the software application 118 to adaptively adjust the duration of the feedback cues 210 and the magnitude or threshold of the condition required for showing the feedback cues 210. If a user 101 is misinterpreting a feedback cue 210 consistently, that specific feedback cue 210 may be suppressed. If the action of a user 101 in response to a feedback cue 210 is correct but lags behind the feedback cue 210, the duration of the respective feedback cues 210 may be extended. Because an extended feedback cue duration may cover more sample images, and because later sample images following the image that generated the feedback cue 210 may have already (through random action on the part of the user 101, intentional action on the part of the user 101, external factors that affect lighting, etc.) made the feedback cue 210 irrelevant or incorrect, the software application 118 may increase the magnitude of the problem or condition required to produce a feedback cue 210 when the software application 118 increases the duration of the specific feedback cue 210. Increasing the required magnitude of the problem or condition required to produce a specific feedback cue 210 may prevent the software application 118 from entering an unstable state due to feedback to and from the user 101.

Referring to FIG. 3, the software application 118 may continue to process the one or more individual images sampled from the live video preview 206, while continuing to display the video to the user 101 along with the graphical aiming cue 204 and real time feedback cues 210, until at least one of several criteria to end the reading session 302 is satisfied. The session 302 may end if a given percentage of the one or more recent images have produced the same OCR partial result 208, in which case the OCR final result string 216 is set to that matching OCR partial result 208 and the session 302 is ended. The session 302 may also end if no such OCR final result string 216 is obtained within a set period of time, in which case the final result string 216 may be set to an empty string (a null result) and the session 302 is ended. In an embodiment, stability and confidence metrics may be determined from the OCR partial result 208. The stability and confidence metrics may lead to the software application 118 adaptively determining the reading does not appear to be leading to a useful result in an acceptable, but not fixed, time period. The software application 118 may then end the session 302. Other situations where the software application 118 ends the session 302 are possible.

The percentage of recent images required to successfully end the reading session 302 may be determined using the one or more configuration parameters 116 specific to the model of external device 106 being read, based on empirical tests. The percentage may be expressed as a number of readings that must match, within a given number of most recent readings. In an embodiment, when reading an Omron 761 blood pressure monitor, five of the most recent ten readings must match in order to choose that matching reading as the successful OCR final result.

The matching reading may also be required to be a "valid" reading to qualify. Valid readings will be discussed below.

Defining the matching percentage based on the model of external device 106 allows the reading of some external devices to converge to a final result more rapidly, while being more conservative with the reading of other external devices. This accounts for some external devices being more difficult to read reliably (e.g. devices with cramped displays) whereas other devices may change their displayed values rapidly (e.g. heart rate monitors). Typical match percentages range from three of the last five images to five of the last ten images.

Figure 8B:
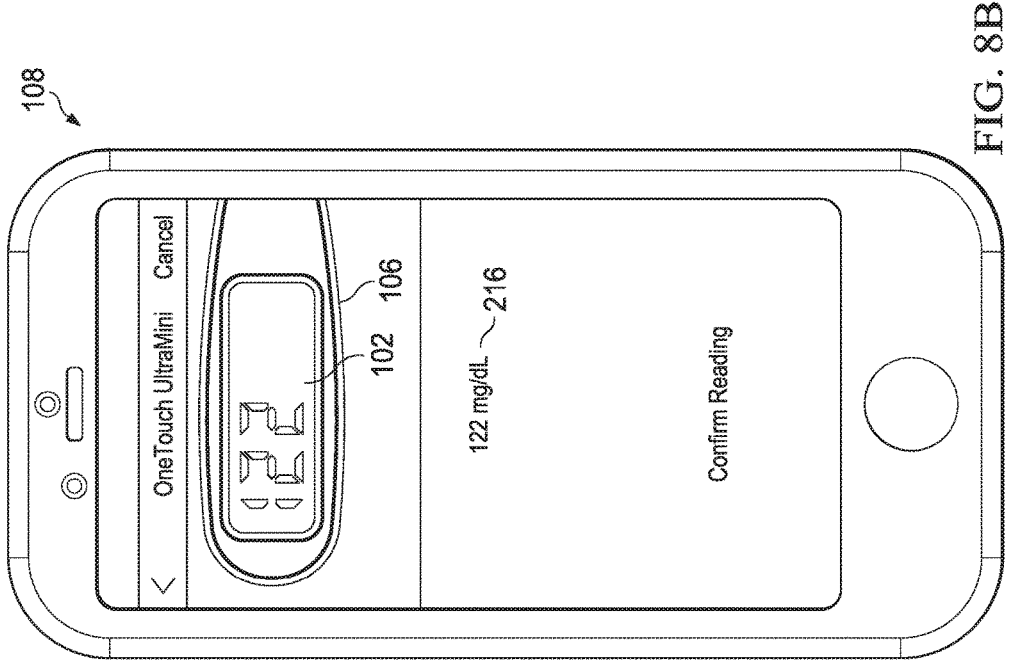
FIGS. 8A and 8B depict results screens of an exemplary application for optically reading an external segmented display.
Figure 8A:
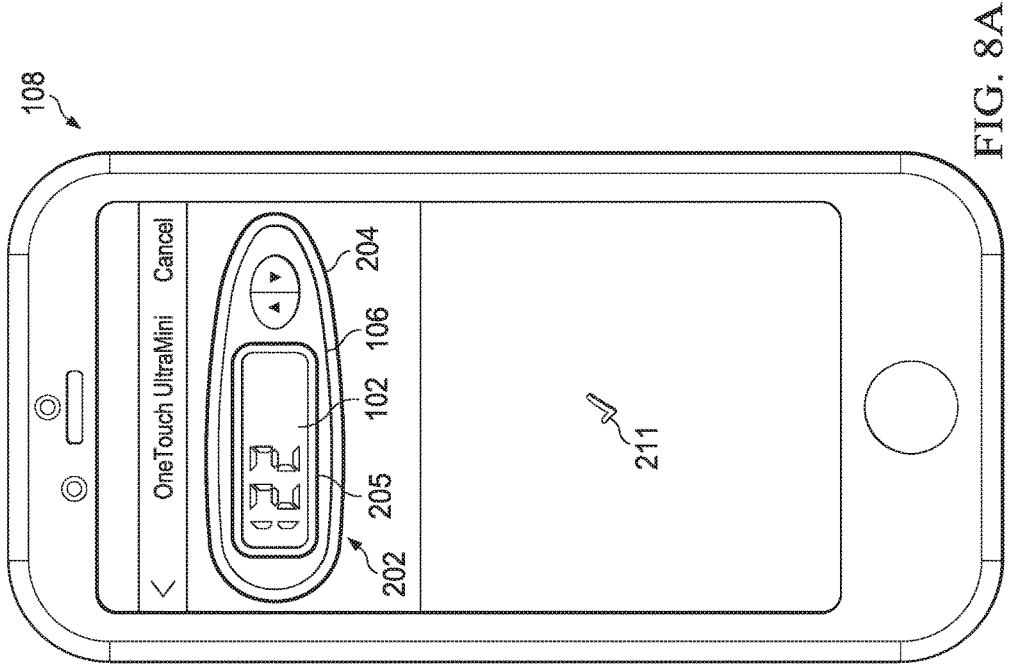

Referring to FIGS. 8A and 8B, if the OCR final result string 216 was successful, a real time feedback cue 211 indicating the success may be briefly shown as seen in FIG. 8A. When the software application 118 terminates a reading session 302, a final result string 216 may be presented on a screen of the software application 118 as shown in FIG. 8B. The user 101 may view and verify the final result string 216.

The display of the final result string 216 may also be accompanied by a confidence rating. This confidence rating may be a simple sum of the errors calculated during image processing (discussed below) when actual segmented display segments detected in the image is compared to their expected location in the image. Larger values for the confidence rating would indicate a weaker result. Other expressions of the confidence rating are possible, such as inverting the segment location error sum in order to associate higher confidence ratings with lower error, factoring in the likelihood of readings in improbable value ranges for real measurements, factoring in the risk associated with values that are empirically determined to be likely sources of errors, etc.

Figure 9B:
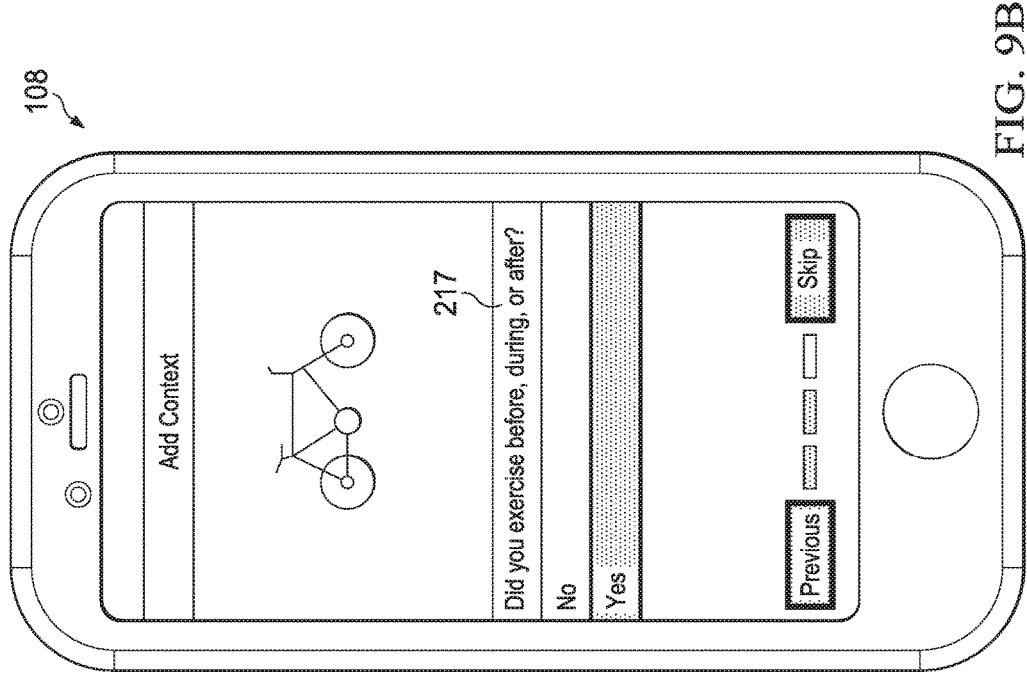
Figure 9A:
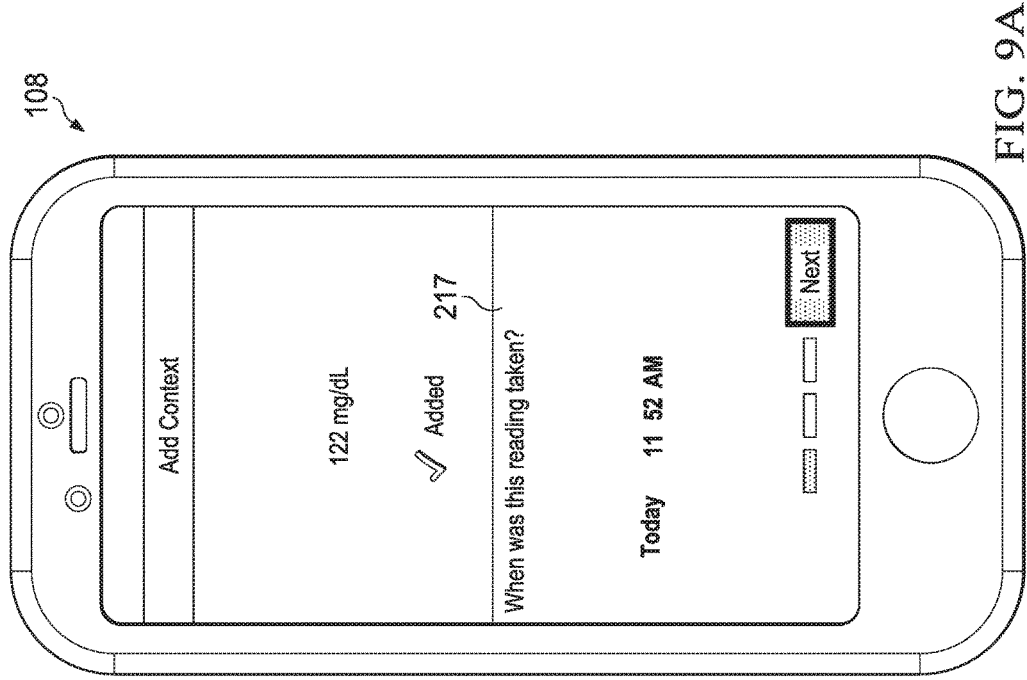

Referring to FIGS. 9A and 9B, when the software application 118 has displayed the final result string 216 to the user 101, the software application 118 may also ask the user 101 survey questions 217. The answers to the survey questions may be used to associate relevant meta-data with the final result string 216. In an embodiment, the user 101 may be asked when the reading was taken. In another embodiment, when a glucose meter is read, the software application 118 asks the user 101 whether the reading was taken before a meal, after a meal, or after exercise. Other useful survey questions 217 are possible.

A variety of uses for the final result string 216 and the associated answers to the survey questions are possible. The final result string 216 and associated answers could be sent across a computer network to a remote server, added to a local database on the reading device 108 containing historical readings, etc. In an embodiment, the final result string 216 and the associated answers are displayed to the user 101 and sent to a remote server 122 for storage and analysis.

Figure 7:
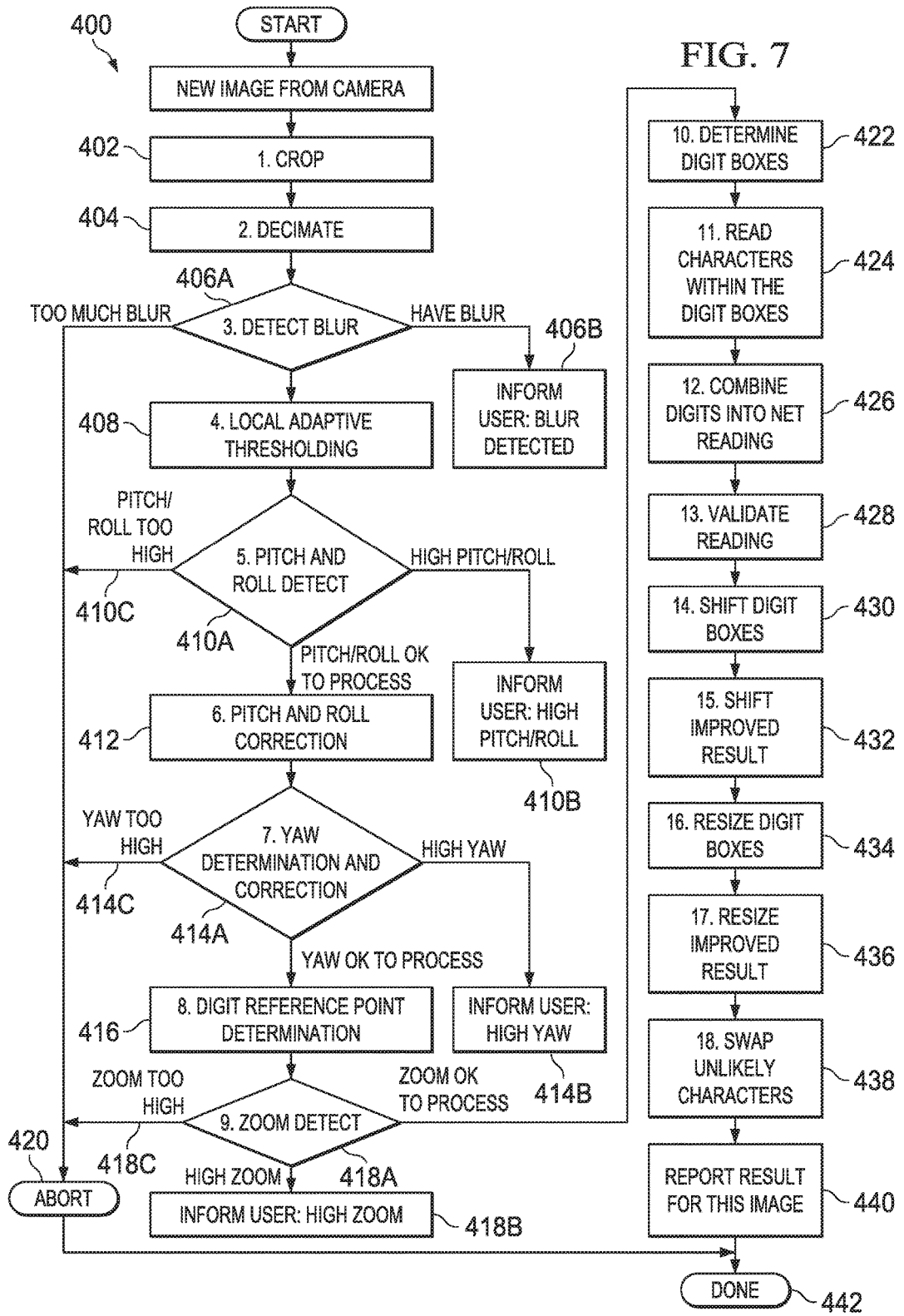
FIG. 7 is a flow diagram for image processing in an exemplary system for optically reading an external segmented display.

Referring to FIG. 7, depicted is a flow diagram for the image processing subsystem 400. The image processing subsystem 400 may process each of the one or more sampled still images via a series of operations on the still image data. These operations may be called the "image processing steps." The software application 118 may call into the image processing subsystem 400 in order to provide the subsystem 400 with the still image data sampled from the live video preview 206 viewed by the camera 110. The software application 118 may then receive a single-image partial result 208 from the image processing subsystem 400, along with flags which are used to determine which user feedback cues 210 the software application 118 should show the user 101. As discussed above, the user feedback cues 210 enlist the help of the user 101 in improving the one or more still images captured and the OCR final result string 216.

Referring to FIG. 10, depicted is an image 401A of a typical LCD/LED device front panel as an example of an external segmented display device 102. The "segmented display panel 102" portion of the image may be defined as the portion of the device image that is defined by the actual LCD or LED hardware, as opposed to other areas of the front panel of a device that may consist of a labeled plastic cover/housing, buttons, etc.

Figure 11:
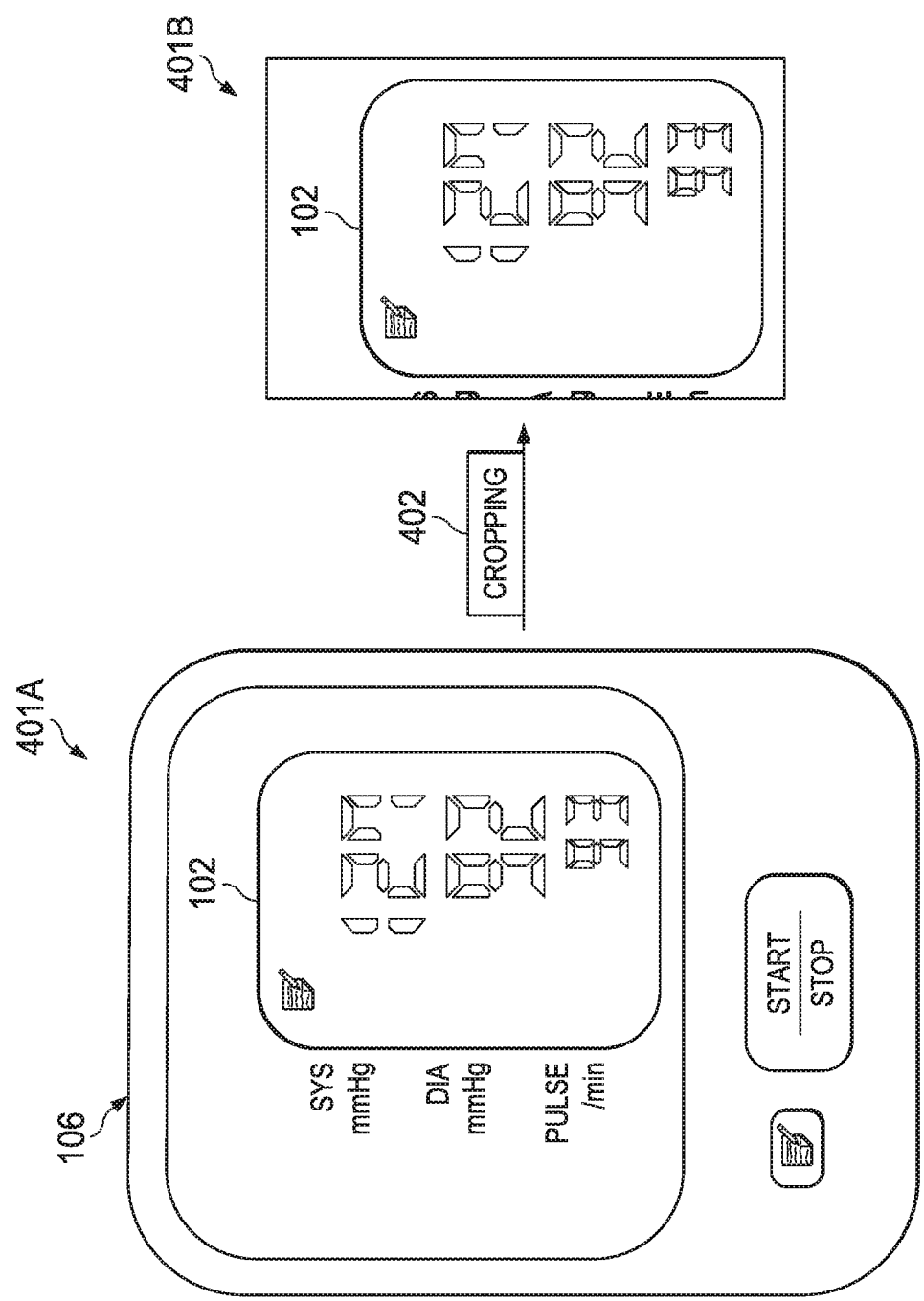
FIG. 11 depicts an exemplary cropping operation.

Referring to FIGS. 5, 7, and 11, the first step in image processing may be cropping 402. In this step, the image 401A may be cropped in a way that interacts with the graphical aiming cue 204 superimposed over the live video preview 206 shown to the user 101. The user 101 may be prompted with the graphical aiming cue 204 on the screen of the reading device 108. The graphical aiming cue 204 may be overlaid onto the live preview video 206. The user 101 may be instructed to aim the graphical aiming cue 204 such that the LCD/LED device panel fits just inside the cue 204, as shown in FIG. 5.

The image 401A may then be cropped to the size of or a certain percentage larger than the effective extent of the graphical aiming cue 204 in the still image 401A. The amount of extra image area included in the cropped image 401B, beyond the extent of the graphical aiming cue 204, may be selected to include the actual display panel extent for most actual still images, taking into consideration the errors of the user 101 in placing the graphical aiming cue 204, hand tremors and other involuntary motions, etc. FIG. 11 shows an example of the image cropping step 402.

Image cropping 402 may be performed by standard means, using local image processing libraries commonly available on mobile phones, PCs, and other devices running the software application 118.

Cropping 402 is preferably performed as early as possible, in order to have as small an image 401B as possible for the computationally expensive later image processing steps. However, the information needed for those later steps should not be cropped off before the later steps are performed. The precise relationship between the geometry of the graphical aiming cue 204 and the cropped area of the image 401B should be set to retain information needed in the later image processing steps. For example, as discussed below, 2D convolution step filters may be used to detect the edges of an external device display panel 102. The display panel edges may be detected by matching the center of a filter to the edge of the display panel. For these filters, it is desirable for the cropped image 401B to include some area beyond the display panel edge; so that the outer half of the step filter has enough pixels to be fully convolved with the image 401B. Additionally, user 101 error in aiming the camera viewfinder may create variation in where the actual display panel appears in an actual image. Therefore, it is desirable to allow for a larger crop area to increase the likelihood the entire display panel actually appears in the image 401B and is sufficiently far from the edge of the image 401B for the edge detection filter convolution.

The extra margin needed around the graphical aiming cue 204 may be determined experimentally in practice with actual users, taking into account a user's tendency to move the camera 110 slightly too close to the image 401B and the user's actual variation in the accuracy of aiming the graphical aiming cue 204.

In an embodiment, the graphical aiming cue 204 is of a fixed size relative to the cropping rectangle. The size of the graphical aiming cue 204 may also be adjusted based on feedback from later steps. For example, the size of the graphical aiming cue 204 may be adjusted based on consistent aiming discrepancies on the part of the user 101.

Figure 12:
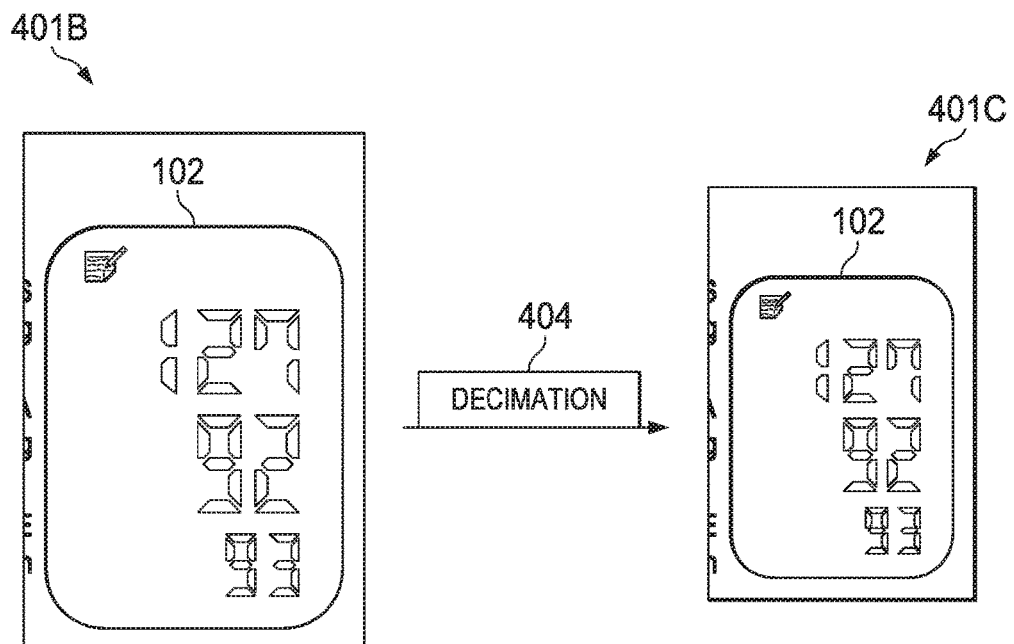
FIG. 12 depicts an exemplary decimation operation.

Referring to FIGS. 7 and 12, the second step in image processing may be decimation 404. Images captured by modern cameras are often very high resolution, e.g. 1920× 1080 pixels ("true" HD). Typical smartphone cameras, for example, have default preview video resolutions equal to or better than HD. However, image processing does not require images of high resolution. Decimation of the image 401B is reduction in the image's resolution. As an example, an image may be decimated so that it is no larger than 356 pixels wide by 480 pixels tall. Like cropping, decimation 404 is preferably performed early in the image processing steps, so that later, computationally more difficult filtering steps can be performed faster on a decimated image 401C.

Decimation 404 may be performed using a standard sub-sampling approach, as is commonly used by local image processing libraries available in most computer operating systems. However, it can be advantageous for the software application 118 to perform the sub-sampling on its own, instead of relying on a library, because the software application 118 may then be able to use multiple threads to accelerate the process. The software application 118 may use as many threads as are available on the reading device 108, for example four threads on a modern "four core" smartphone CPU. For reading devices that natively sub-sample the image to specification in the reading device's image capture subsystem, a separate decimation operation is not needed in the software application 118 itself. FIG. 12 shows an example of the decimation step 404.

Other, more complex decimation strategies are possible, such as averaging. These decimation strategies might improve the outcome of the reading by reducing small-scale noise or in other ways. However, more complex decimation strategies also have the additional cost of being more computationally expensive. Simple sub-sampling has the advantage of a low computational cost.

Referring to FIG. 7, the third step in image processing may be blur detection 406A. Blur detection 406A may be achieved by using standard algorithms, but other methods are possible.

As an example, a typical approach for blur detection 406A is to perform an edge sharpness analysis, by reckoning the distribution of pixel intensity gradients for the entire image 401C, and then judging distributions with low mean values or high standard deviation as being blurry. Another common approach is to use that same distribution of pixel gradients to construct a Bayes discriminant function, and use the discriminant function to classify the image 401C as blurry or sharp. Blur may also be detected as a deficit of high frequency motion energy, as blurry images can make it impossible to resolve the motion of small features in the image subject.

If problematic blur is detected, a real time feedback cue 210B may notify the user 101 via the user interface of the software application 118 and may warn the user 101 that blur is present. The user 101 may adapt by shifting the camera 110 (e.g. moving the smartphone) to allow for proper focus. The degree of blur may also determine whether the image processing subsystem 400 should proceed with further processing to detect numbers and text. If there is too much blur, the image processing system 400 may not proceed further.

Figure 13:
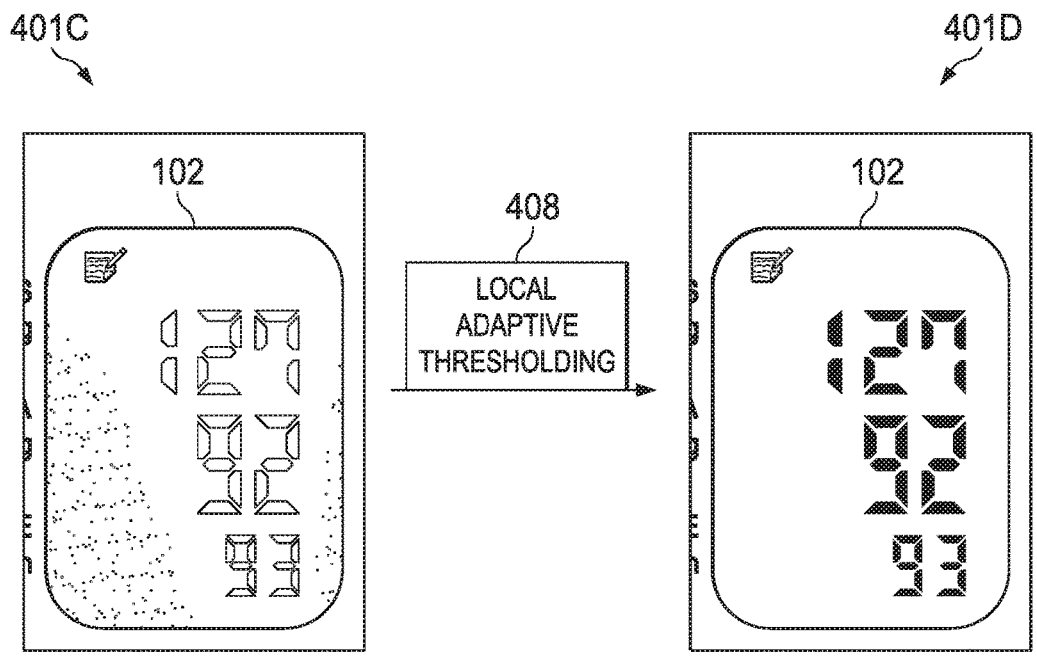
FIG. 13 depicts an exemplary Local Adaptive Thresholding (LAT) operation.

Referring to FIGS. 7 and 13, the fourth step in image processing may be Local Adaptive Thresholding (LAT) 408. LAT 408 is a standard technique for converting grayscale images (having a range of possible values per pixel e.g. 0 to 255) into binary pixel black and white images (having only two possible values per pixel, black, or white). The cropped and decimated image 401 may be thresholded via LAT 408 before further processing is done. LAT configuration parameters, such as LAT filter size and final subtracted constant magnitude, may be set on a per-device-model basis, using values experimentally determined to be optimal for each actual device model (or similar models). FIG. 13 shows an example of the LAT step 408.

LAT 408 is conventionally performed on grayscale images, but for typical cameras, the image 401 captured from the video preview screen is a multicolor image. For example, a typical smartphone camera image consists of red, blue, green, and alpha/opaqueness values (RGBA). The image processing subsystem 400 may use only one color channel of the multicolor image 401 as input to its LAT calculation. The channel chosen may vary depending on the external device model. The color characteristics of the LCD/LED screen of the external device model may determine the color channel chosen.

LAT 408 is typically computationally expensive, involving summing pixel values across many pixels (e.g. hundreds of pixels) in order to determine the LAT output value for each individual pixel (LAT is based on exceeding the local average by a set amount). For this reason, several efficiency improvements may be made to the LAT calculation, interlaced with later image processing steps. Instead of performing LAT 408 all at once on the entire image up front, LAT 408 may be performed just-in-time for each pixel when the pixel is first examined for use in a later stage of image processing.

Furthermore, many subsequent image processing steps may be searches in which a series of adjacent pixels are examined, one by one, in order. The image processing subsystem 400 may leverage this process by caching the LAT sum as a partial result for each neighboring pixel, and adjusting that sum to compensate for moving over one pixel. This caching and adjusting may reduce the calculation time exponentially. For example, for a LAT filter width of 15 pixels the reduction may be a factor of 15.

The just-in-time calculation of thresholded pixel values via LAT 408 may be amenable to multi-threaded reckoning (for use in multi-threaded image processing steps detailed elsewhere in this disclosure) through use of a thread-safe atomic flag per pixel that indicates whether the thresholded value is already available, e.g. through work done in another computer processing thread.

In subsequent discussions of later steps of the image processing subsystem 400, it should be understood that each pixel examined during that processing may be thresholded via LAT 408 just in time for its first use in any calculation.

The most common LCD displays show dark characters on a gray or white background, but some LCD displays show white or light gray characters on a black or dark gray background. These light-on-dark "inverted" LCD displays are effectively inverted with respect to the more common dark-on-light LCD displays.

LCD displays most naturally show a dark colored LED lit character on a light background. For the image processing subsystem 400 to handle both situations, the LAT algorithm may be adjusted to yield a dark on light binary output in both cases. For inverted LCD displays (originally light characters on a dark background), the LAT algorithm may be adjusted to invert the sensing of the threshold. The average of nearby pixel values forms a threshold, but the pixel being examined may be tested for being lower than the threshold by a configured amount (ordinary non-inverted displays may be tested for a pixel being greater than the threshold). If the pixel in question is lower than the threshold, it is marked as a dark pixel in a (now effectively inverted) output image. Otherwise, the pixel in question is marked as a light pixel in the output image that is passed to the next step of image processing.

Figure 14B:
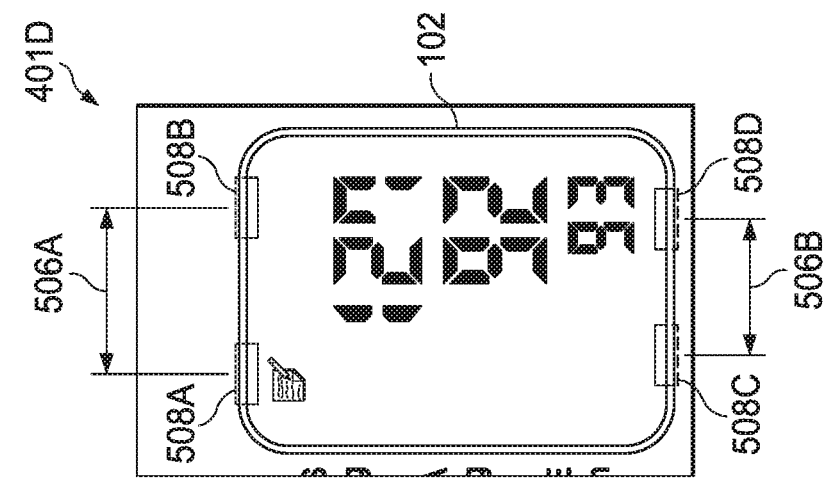
FIGS. 14A and 14B depict exemplary pitch and roll detection operations, respectively.
Figure 14A:
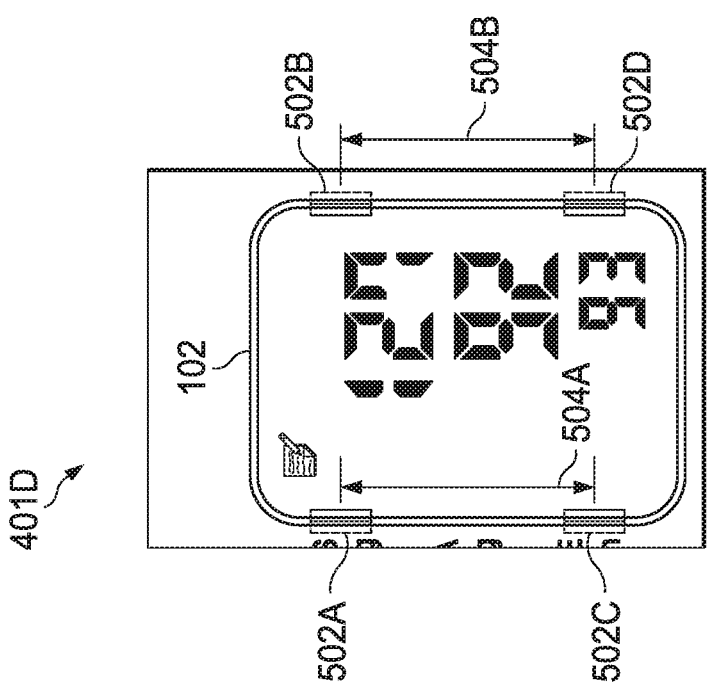

Referring to FIGS. 7, 14A, and 14B the fifth step in image processing may be pitch and roll detection steps 410A. In practice, the user 101 may not orient the camera 110 (e.g. on a smartphone) precisely with respect to the housing or panel of the external device 106 (or to its tangent, for curved panels/housings). Fortunately, the degree of pitch and roll can be estimated and corrected prior to attempting to read the text on the display. FIG. 14A shows an example of the pitch detection step of the pitch and roll detection 410A.

The image processing subsystem 400 may use a standard technique for assessing pitch as shown in FIG. 14A. The image processing subsystem 400 may detect four features 502A-D in the image 401D and use those four features 502A-D as reference points to draw two nominally vertical lines 504A, 504B. If the resulting lines 504A, 504B are parallel, there is no pitch. If the resulting lines 504A, 504B are closer together at the top, the image is pitched "forward," etc. For segmented displays, the features 502A-D detected may be the edges of the external device LCD/LED display panel. Other feature detectors are possible, such as corner detectors, spot detectors, etc.

Figure 19:
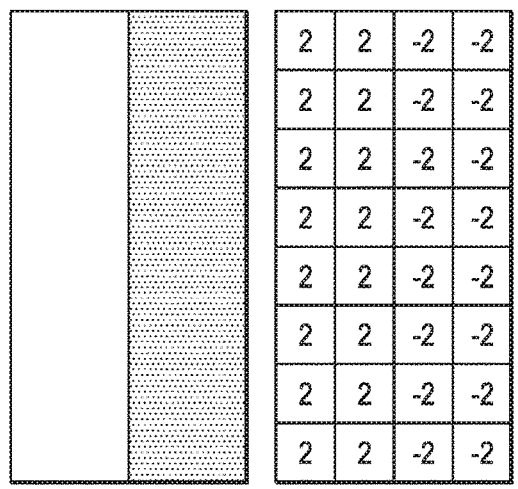
FIG. 19 depicts an exemplary 2D convolution step matched filter for edge detection.

Referring to FIGS. 14A and 19, the edges may be detected using a 2D convolution step matched filter for edge detection, with a simple high/low edge detection filter. The convolution may be treated as a correlation value, such that a portion of the image that resembles an edge facing the correct direction has high correlation. Such 2D edge detection filters may be used in later image processing steps as well. Whether an external device display panel edge or an external device housing edge is used as the image rotation edge may be configured depending on the model of external device 106.

Referring to FIG. 14A, to find the edge of the display panel 102 or housing, two points along the relevant border may be detected by searching from the center of the image 401D outward along two separate lines. The device housing/panel border may be detected as the maximum correlation output from 2D image convolution along a given line. These two separate points may correspond to a line for which there is a configured expected relationship to the geometry of the overall device display. These two separate points may be the output passed to the next step of the pitch detection.

The simplest features for orienting the image may be linear "straight" edges in the image 401D. However, in order to accommodate irregularly shaped features useful for orienting the image 401D, the image processing subsystem 400 may use combinations of 2D convolution edge detection filters arranged to match the feature's edge contours. Referring to FIG. 14A, the image processing subsystem 400 may search for a diagonal edge using a series of sub-filters distributed along the desired diagonal. If a curved contour is expected due to the external device model, the image processing subsystem may use a series of individual linear edge detectors, arranged in a curve. The summed convolution-generated correlation from all filters in the series may be maximized to estimate the edge location. Other 2D convolution edge detection filter arrangements that would detect other edges, including edges that curve back onto themselves, are possible.

Edge detection may be multi-threaded, as the edge detection of each of the two points along each edge feature may be performed independently. In an embodiment, two threads are used, one for each point detected on an (as yet undetected) side. It is possible to decompose each side's detection into two threads (one for each point detected on each side) or even more threads (dividing up the search along each line, so that part of the search area is processed by each of an arbitrary number of threads). On systems with a graphics processing unit (GPU) capable of a high degree of parallelization of selected operations, including convolution of simple filters, it is possible to use massively parallel implementations of this approach.

Other features could also be detected in order to obtain reference points for assessing pitch and other geometric characteristics of the image 401D, as well as other orientation assumptions about the detected features (e.g. assumed vertical instead of horizontal) and other filters that could be convoluted with the image 401D at relevant sample locations in order to detect those features.

Referring to FIGS. 7 and 14B, the fifth step in image processing may also include the roll detection step of the pitch and roll detection 410A. The image processing subsystem may assess and correct roll in the same way that it assesses and corrects pitch, but using two horizontal lines 506A, 506B (defined by four image features 508A-D) instead of the two vertical lines 504A, 504B used for pitch detection. FIG. 14B shows an example of the roll detection step of the pitch and roll detection 410A.

Referring to FIGS. 7, 14A, and 14B, the sixth step in image processing may be pitch and roll correction 412. Pitch and roll correction 412 may be a simple stretching of the image 401D, proportional to the distance from the "wide" side of the image 401D. The pitch and roll may each, separately, be compared to two configured thresholds.

Referring to FIG. 7, the first, smallest threshold may be the threshold for sending feedback 410B to the user 101 about the pitch/roll. Referring to FIG. 6E, if the image shown in the video preview stream 206 is rolled right more than the defined threshold, the user 101 may be shown a graphical feedback cue 210E to roll the camera 110 to the left, and vice versa. Referring to FIG. 6D, if the image shown in the video preview stream 206 is excessively pitched "forward" (top to bottom); the user 101 may be shown a graphical feedback cue 210D to pitch backward, and vice versa.

As the images are being processed in real time, the pitch/roll estimates may be available on a per-frame basis many times per second. The software application 118 may separately determine how long to display the pitch/roll indications 210D, 210E to the user 101. Displaying the pitch/roll indications 210D, 210E for one frame's worth of time, typically only a fraction of a second, would ordinarily not give the user 101 enough time to understand the instruction. For this reason, the software application 118 may detect that the image has, for multiple successive images, been rolled or pitched beyond a configured tolerance. In response, the software application 118 may then show the graphical cue 210 via the user interface. The graphical cue 210 may direct the user 101 to adjust the roll/pitch. To give the user 101 time to understand the instruction, the graphical cue 210 may be shown for a minimum of a full second.

Referring to FIG. 7, the second, higher threshold may be the threshold for aborting the image processing loop. If the image is sufficiently pitched or rolled, further processing is risky, and a highly uncertain reading may result. When this condition 410C is detected, the user 101 may be warned via the previously explained graphical cues, and the image processing may be aborted.

Referring to FIG. 7, regardless of the indications shown to the user 101, if image processing is not aborted due to excessive pitch/roll, the image may then be automatically adjusted to correct the pitch/roll. The correction 412 may be performed using a standard sampling algorithm that expands the portions of the image that are (relatively) compressed. The expansion may be applied as a gradient from one side of the image to the other, via interpolation with respect to the two sampled distances, and the corrected image may be passed on to further stages of image processing.

Pitch and roll detection 410A and correction 412 are generally computationally expensive. Depending on the computational power of the reading device 108 and available performance enhancements, the increased yield in overall system performance may not justify the expense. Therefore, it may be desirable to omit pitch and roll detection and correction.

Referring to FIG. 7, the seventh step in image processing may be yaw (also known as skew, or rotation in the plane of the image) determination and correction 414A. Referring to FIGS. 14A and 14B, if pitch and roll detection is performed, yaw may be simply detected as the rotation of one of the pitch/roll reference lines 504A, 504B, 506A, 506B with respect to its expected position.

Figure 15B:
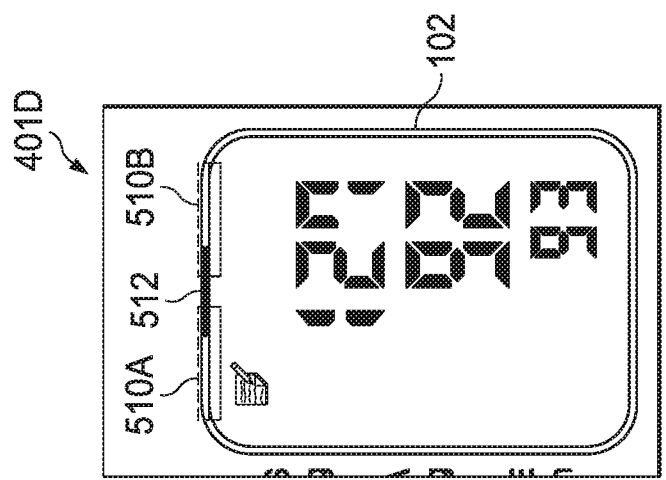
FIGS. 15A and 15B depict exemplary yaw determination and correction operations, respectively.
Figure 15A:
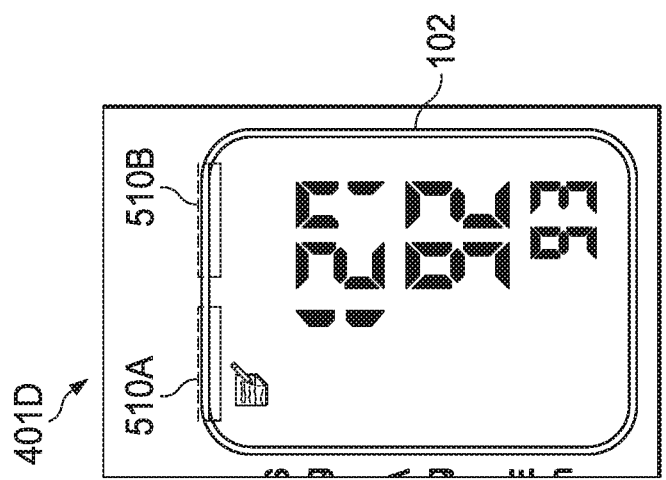

Referring to FIGS. 15A and 15B, if pitch and roll detection 410A are omitted, yaw may be detected by performing a subset of the pitch detection step of pitch and roll detection 410A. A single horizontal edge of the segmented display 102 may be detected at two locations via 2D edge detection convolution filters. The resulting two points 510A, 510B may be used to form a "yaw line" 512 which is corrected against the expected horizontal value to fix yaw problems in the image. For some devices, the top edge of the display panel 102 is more reliable. For some others, the bottom edge is more reliable. On other devices, the left edge is more reliable or the right edge is more reliable. The image processing subsystem 400 may be configured with empirically defined preferences, depending on the external device model, for which edge to use to determine the yaw. Additionally, in place of a display panel edge, another linear edge feature which is reliably present may be used. For example, on some external device models the segments themselves may be the best choice. Most LCD/LED displays reliably have at least one vertical LCD/LED segment in each digit, and on some displays the display panel edges may be much harder to detect than the segments themselves.

Referring to FIG. 15B, yaw may be easily corrected by conventional means. The image processing subsystem 400 may rotate the image by trigonometrically selecting a corresponding original image pixel location for each rotated output image pixel location, and copying the original pixel into the rotated pixel location of the output image. The sample from the original image may be taken to be the nearest pixel to the trigonometrically correct position that should be the source of the output rotated image pixel. However, one skilled in the art could create other sampling methods employing interpolation, local averaging, etc.

Rotation is generally a computationally expensive operation. For this reason, the image processing subsystem 400 may not perform rotation if the image is less than one degree out of line. Such a rotation is unlikely to significantly affect the subsequent operations.

If the yaw is too high, then the software application 118 has likely encountered an error condition. In this situation, the image processing subsystem 400 may abort 414C the processing of the image in order to avoid a poor "garbage in, garbage out" result.

The image rotation may be multi-threaded, as the resampling of each pixel can be performed independently. Parallelization of this step can use as many threads as are available from the operating system 114, up to the number of pixels in the display image.

Figure 6C:
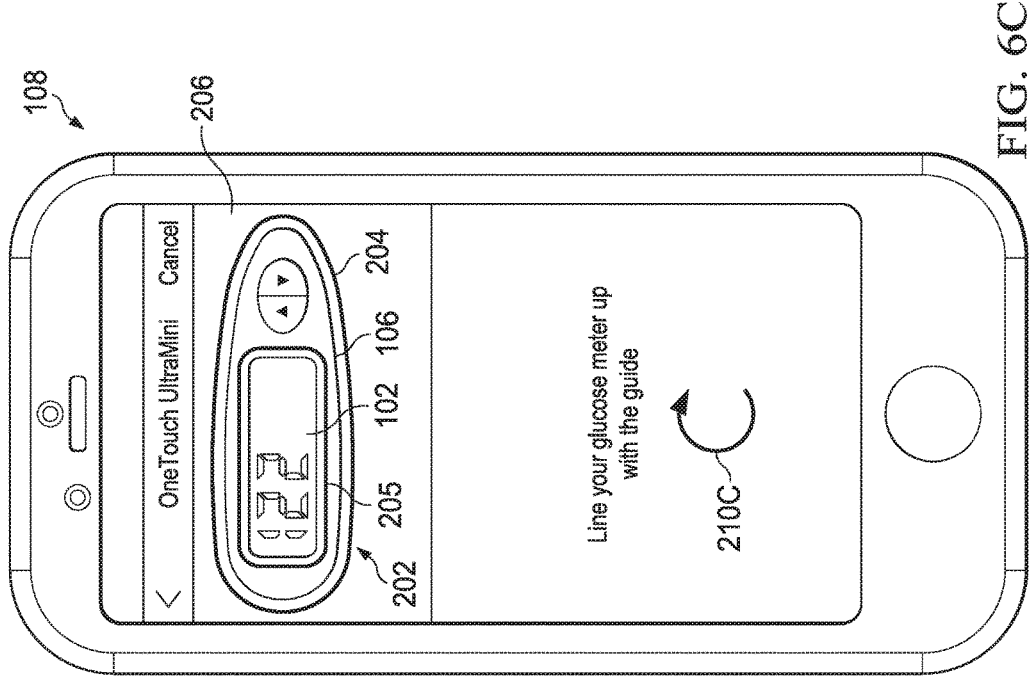

Referring to FIG. 6C, if the image processing subsystem 400 detects yaw, a real-time graphical indication 210C may be shown to the user 101 via the user interface of the application 118, to warn the user 101 that the image is seen by the software application 118 as being out of alignment. Though the image processing subsystem 400 also attempts to correct the rotation, the user 101 can profitably help by correcting at least some of the rotation before the image processing subsystem 400 has to deal with it. In this way, the user 101 can in some cases avoid having any rotation performed by the image processing subsystem 400, which can lead to a more efficient and therefore quicker result.

Referring to FIGS. 7 and 16A, the eighth step in image processing may be digit reference point determination 416. After any applicable pitch, roll, and yaw correction, the image processing system 400 may generate the "digit reckoning reference point" 520—a reference point which may later be used to set expected positions for the LCD/LED digits in the image. The digit reckoning reference point 520 may be the intersection of a pitch line 502A-D and a roll line 508A-D from the previous pitch and roll detection steps 410A. The pitch line may be the left pitch 504A or the right pitch line 504B, and the roll line may be the top roll line 506A or bottom roll line 506B. The most reliably detected display panel edges for the external device model may be used for the intersection.

As shown in FIG. 16A, if the pitch and roll detection steps 410A are omitted, the image processing subsystem 400 may detect the left side 514 of the external device display panel 102 using (again) a 2D edge detection convolution filter. The image processing subsystem 400 may then use the intersection of that line 514 with the yaw line 512 as the digit reckoning reference point 520. The left side may be detected as one point (rather than two points, as was discussed with respect to roll detection). The image processing subsystem 400 may assume that, as the yaw has already been corrected, the left side 514 is perfectly vertical and therefore defined by the one detected point.

Referring to FIG. 7, the ninth step in image processing may be zoom detection 418A. The image processing subsystem 400 may assess the zoom level of the image—how much larger or smaller the image is than the expected size. The distance between the two vertical pitch lines 504A, 504B may be taken to be the width metric for zoom assessment. Referring to FIG. 14A, after correction, lines 504A, 504B should be practically vertical. The distance between the two corrected horizontal roll lines 506A, 506B may similarly be taken to be the height metric for zoom assessment.

The height metric may be compared to an expected value (for the model of external device) to form a height zoom ratio. Similarly, the width metric may be compared to an expected value (for the model of external device) to form a width zoom ratio. If the features used to define the pitch and roll lines 504A, 504B, 506A, 506B were correctly detected, the height zoom ratio and the width zoom ratio should be the same.

If they are not, a most trusted metric for the model of external device 106 is used. This most trusted metric may be the height metric or the width metric, and may be determined empirically for each model of external device. In later image processing steps, the resulting zoom ratio may be applied to all expected positions in the image.

Referring to FIG. 16A, if the pitch and roll detection steps 410A are omitted, the image processing subsystem 400 may use a single 2D convolution edge filter to find the right edge 516 for comparison to the left edge 514 previously found in determining the digit reckoning reference point 520. The distance from this right edge 516 to the previously determined left edge 514 position compared to its expected value (for the model of external device) for an image of nominal zoom may be used as the width zoom ratio. For the height zoom ratio, one border of the external device display panel 102 may already have been previously found from the yaw detection step 414A. The other side of the segmented display panel 102 may be found using a single 2D convolution edge filter. The distance between the two may be compared to its expected value (for the model of external device) to generate the height zoom ratio.

Note that, if yaw correction has already been performed and pitch and roll are assumed to be negligible, the top and bottom of the segmented display panel 102 may be assumed to be horizontally oriented. Therefore, the top and bottom of the segmented display panel 102 may be assumed to require only one point to assess.

After the image processing subsystem 400 determines the zoom ratio, the software application 118 may use this information to interact with the user 101 in real time and improve the result. The display panel zoom (as estimated) can be too large or too small for reliable calculations in later image processing steps. There may be two configurable tolerances for this determination—the variance from the desired external device display panel size (for each dimension) at which reliable processing in later stages is threatened, and the variance at which reliable processing is abandoned.

Figure 6F:
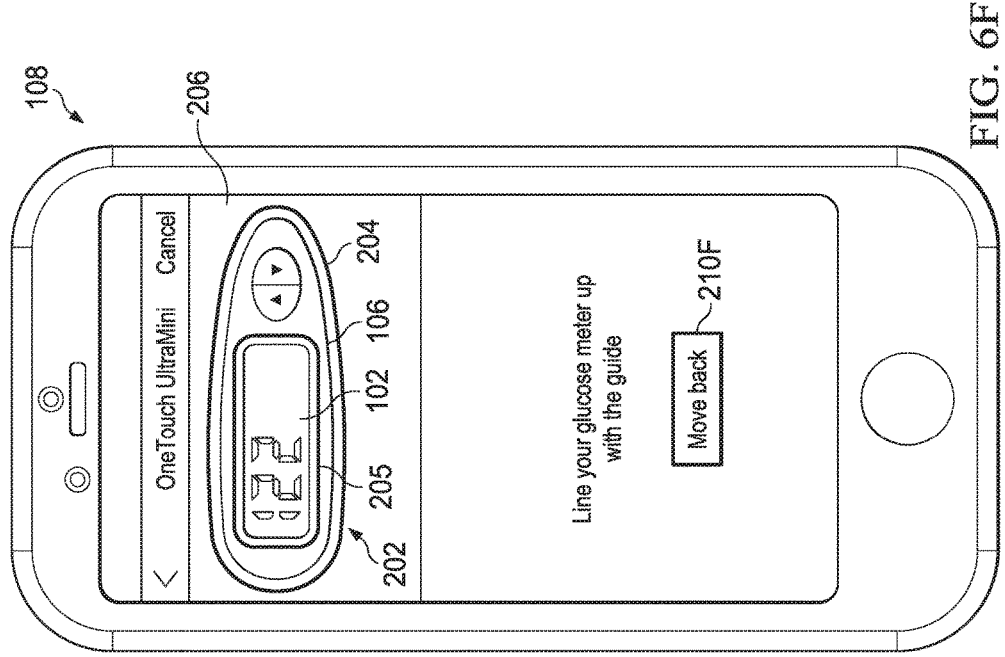
Figure 6E:
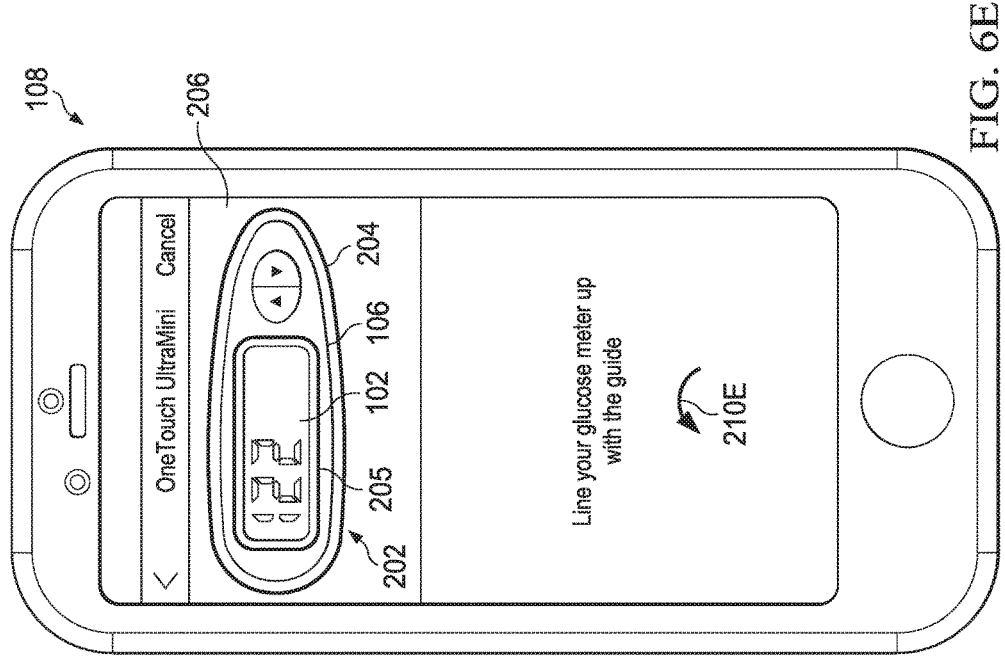
Figure 6H:
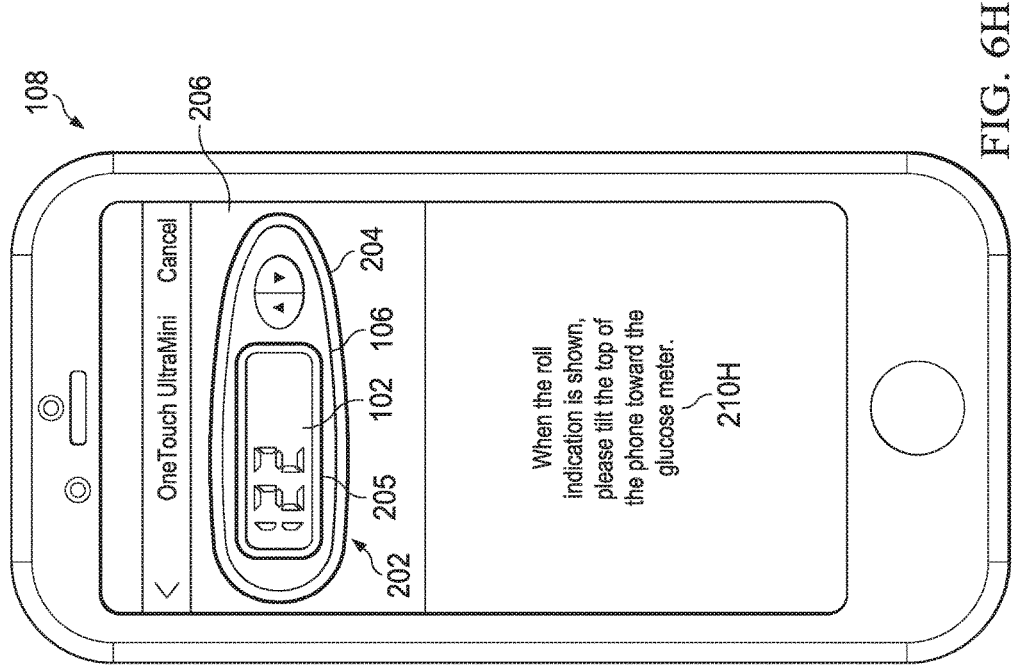
Figure 6G:
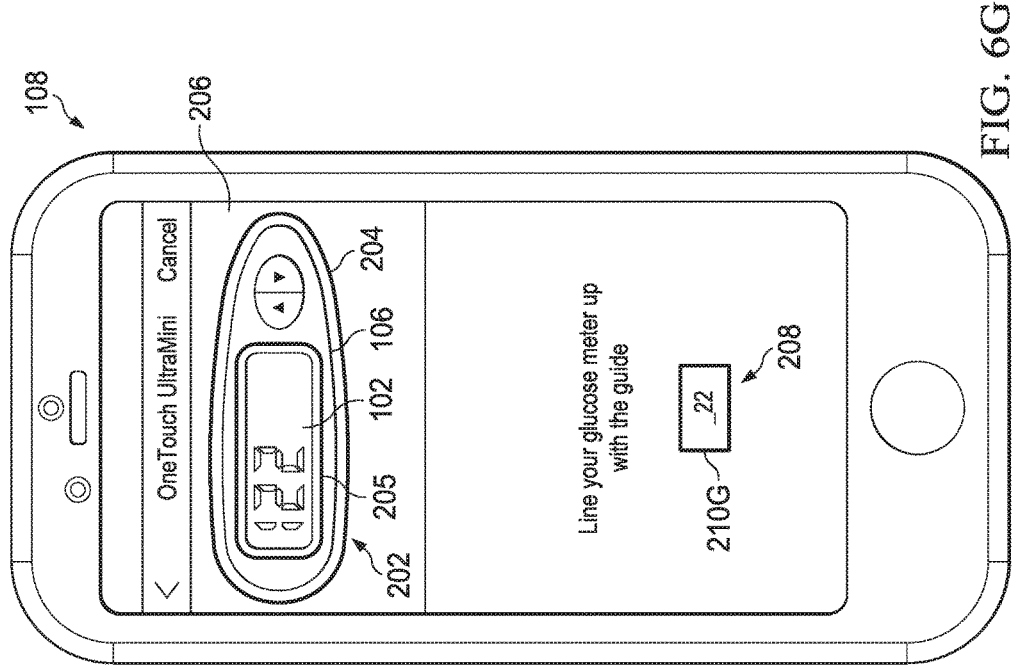

Referring to FIGS. 6F and 7, the software application 118 may show the user 101 a "zoom in" or a "zoom out" feedback cue 210F when the first tolerance is exceeded, but continue with the remaining image processing steps. If the second, more dangerous tolerance is exceeded, in addition to displaying the feedback cue 210F further image processing may be aborted. Aborting further image processing may avoid wasting valuable processing effort that would only generate a highly uncertain outcome.

As with the overall size (magnitude) of the estimated display panel bounds, there may be tolerances configured for the variance from the expected height-to-width aspect ratio (the width zoom ratio discussed above vs. the height zoom ratio discussed above). Referring to FIGS. 6F and 7, if the difference between the height zoom ratio and the width zoom ratio exceeds a configured tolerance, the user 101 may be notified in step 418B to adjust the camera 110. If the difference between the height zoom ratio and the width zoom ratio exceeds cannot be adjusted, further image processing may be aborted at step 418C.

As with indications for perspective corrections, the indications for zoom corrections 210F may be displayed for more than the duration of one video preview frame, even when only one image is detected to have this issue. Displaying the indications for zoom corrections 210F longer may give the user 101 time to understand the physical correction the user 101 is requested to make, and may close the image-processing-to-user-to-image-processing feedback loop.

Referring to FIGS. 7, 16B, and 16C, the tenth step in image processing may be determining the expected location 422 of the individual segmented numbers (or alphanumeric characters) to be detected. The image processing subsystem 400 may determine "digit boxes" 518, rectangles that are estimated to contain each character. While the rectangles are referred to as digit boxes 518, their contents are not necessarily limited to digits. Digit boxes 518 may contain any character represented in the segmented display 102.

FIGS. 16B and 16C depict the determining of the individual digit boxes 518. FIG. 16B shows the digit boxes 518 in a first area determined. FIG. 16C then shows the digit boxes 518 on the rest of the segmented display 102 determined. The initial estimate of the digit boxes 518 may be based on the previously determined digit reckoning reference point 520. For each model of external device 106, the software application 118 may know a priori the expected position of the characters to be read relative to the digit reckoning reference point 520. The software application 118 may store these relationships for each device model in a database as part of the configuration parameters 116. The relationships may be expressed as a position (upper left corner), width, and height in pixels of the rectangle containing each character, versus the digit reckoning reference point 520.

Using the stored relationships, the image processing subsystem 400 may calculate the locations of the digit boxes 518. The previously calculated zoom ratio may be applied when using the stored relationships. The digit boxes 518 may be stored in the memory of the image processing subsystem 400 for use in later processing steps.

Due to partially or entirely uncorrected perspective distortions of the image 401D, the apparent aspect ratio of the characters in the image 401D may not be the same as the nominal aspect ratio that would be observed if the image 401D was taken with the camera perfectly aligned. For this reason, the image processing subsystem 400 may express the character bounds width in terms of the width of the segmented display panel 102, and likewise the character bounds height in terms of the height of the segmented display panel 102. Thus, when, for example, the apparent width of the display 102 is compressed due to left-to-right rolling of the external device 106 and its display 102 with respect to the camera, the character bounds width may be adjusted accordingly, independent of any height adjustments.

However, the physical characteristics of the display 102 and housing of some external devices may cause the assessment of one dimension of the display to be much more reliable than the assessment of the other. For example, for some external device models, display height may be more reliable than display width. For such device models, the configuration parameters 116 in the software application 118 may specify the character bounds in terms of the more reliable display dimension.

The image processing subsystem 400 may use the more reliable display dimension to calculate both the height and width of the character bounds. This approach sacrifices some adaptability to pitch/roll in favor of using the more reliable display dimension as a sizing metric.

For external devices where the software application 118 is configured to use this approach, if the less reliable display dimension is determined to be outside an aspect ratio-based tolerance with respect to the more reliable dimension, then the more reliable display dimension may be used for all calculations that depend on the display dimension. As an example, if height is more reliably detectable than width on a given external device, and if a particular image of that device is estimated to have a display width that is much greater than expected given the estimated height of the display (exceeding a configured threshold), then the height of the display may be used to calculate the character bounds height and width. Otherwise, if the width is within tolerance with respect to the display height, the display width may be used to calculate the character width and the display height may be used to calculate the character height.

The image processing subsystem 400 may support multiple lines and multiple displays on an external device 106. For example, blood pressure meters typically have three-line displays for displaying systolic pressure, diastolic pressure, and heart rate. The configuration parameters 116 for each model of external device 106 may contain digit boxes 518 positioned on multiple lines. Each digit box 518 may be positioned relative to the display panel bounds, and may be above, below, etc. other digit boxes 518. Each individual digit box 518 may be independent. Digit box 518 positions may overlap, due to allowances for noise, glare, and other flaws in actual images. For each device model, the position of each individual character to be read by the image processing subsystem 400, relative to the display boundary, may be in separate configuration parameters 116. In addition to supporting multiple line displays, this approach may also support displays in which individual characters are displayed in irregularly distributed locations in addition to or in place of orderly rows of characters.

Figure 17B:
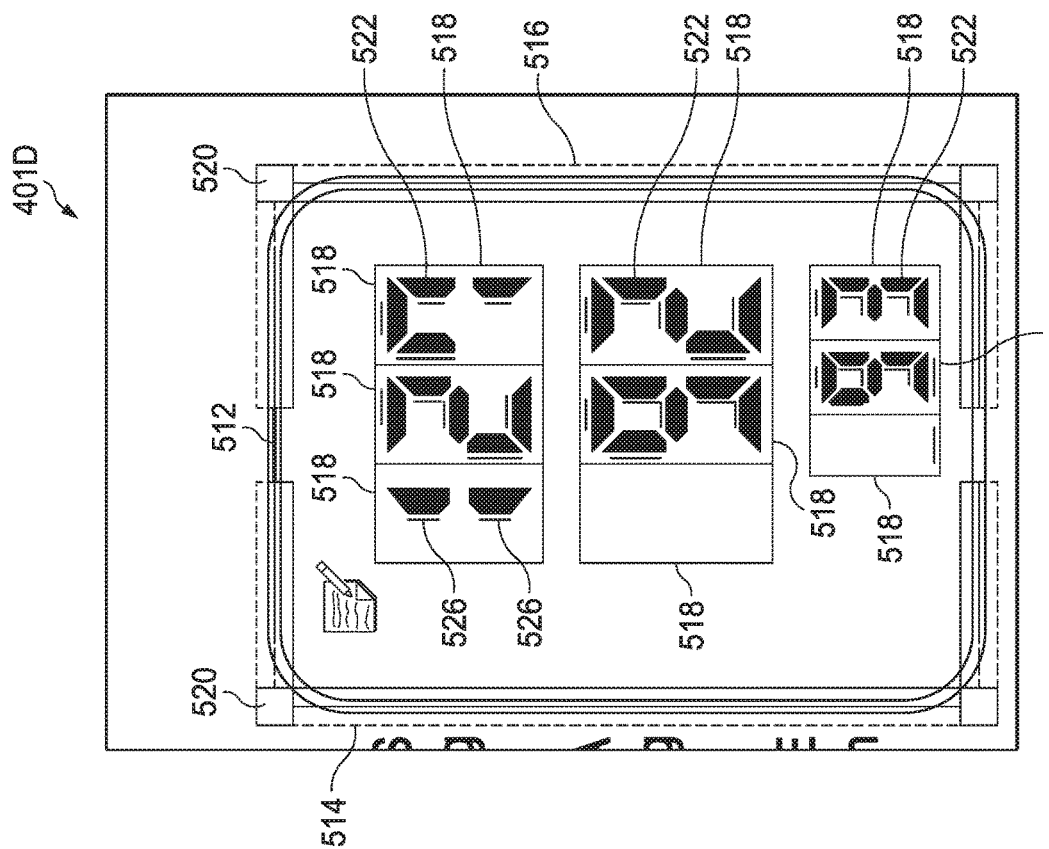
FIGS. 17A and 17B depict exemplary digit segment finding operations.
Figure 17A:
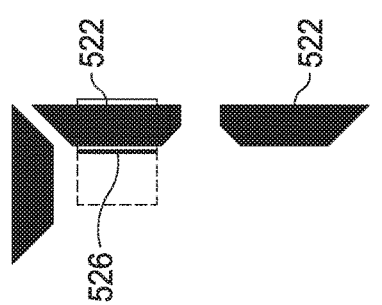

Referring to FIGS. 7, 17A, and 17B, the eleventh step 424 in image processing may be examining the digit boxes 518 to read characters 524. Within each digit box 518, the image processing subsystem 400 may search for individual segments 522 of the segmented display 102 for a character 524. Each segment 522 may be searched for independently as a multi-threaded operation, using a separate thread for each segment 522. For example, for a seven-segment display the image processing subsystem 400 may have seven separate threads. Further parallelization may be possible, as each position in the display 102 may be separately evaluated for the presence of a segment 522.

As shown in FIG. 17A, the segments 522 may be searched for via the same standard 2D convolution edge detection filter correlation method used to search for the sides of the display panel 102. However, smaller 2D filters may be used in order to detect the smaller individual character segments 522. As shown in FIG. 17B, for each segment 522, a centerline may be drawn through the area to be searched along the direction to be searched. The 2D filter may be moved along the centerline, testing for 2D convolution correlation. If sufficient correlation is obtained, the current position may be marked as a location 526 of a segment 522, and the search for that segment 522 may be complete.

Some segmented displays may have diagonal segments at any angle. Even typical seven-segment displays often have a slant to their "vertical" segments 522. The image processing subsystem 400 may handle diagonal segments by simply using a diagonally oriented 2D filter. The diagonal filter for segment detection may be constructed similarly to the diagonal filter previously discussed for the display edge panel detection, as a series of sub-filters distributed along the desired diagonal.

In an embodiment, vertical segments are searched for left to right, and horizontal segments are searched for from top to bottom. Other search patterns are possible, such as bottom to top for horizontal segments.

Due to noise, glare, and other image variations, the digit box 518 is usually not perfectly aligned with the image. If this variation causes a segment 522 to be positioned so that it partially overlaps the edge of its digit box 518, the segment 522 may not be detected depending on the search pattern. For example, when searching left to right for a vertical segment, if the segment 522 overlaps the right edge of the digit box 518, the segment 522 may still be detected because its left hand edge is within the digit box 518. However, if the segment 522 overlaps the left edge of the digit box 518, the segment 522 may not be detected. Therefore, depending on the search pattern and device model, the image processing subsystem 400 may bias its positioning of the digit boxes 518 to account for these inaccuracies. A left to right search direction for vertical segments may lead to a bias causing the digit boxes 518 to be positioned left of where they would otherwise be. Similarly, a top to bottom search direction may lead to a bias causing the digit boxes 518 to be positioned above where they would otherwise be. The direction and degree of bias in the positioning of the digit boxes 518 may be an empirically determined factor, based on measured trends in digit locations in real images. The direction and degree of bias for a device model may be in the configuration parameters 116 for that device model.

A segment 522 may be determined to have been found when the 2D convolution correlation exceeds a configured threshold at several adjacent points. The correlation threshold may be configured per device model, and may depend on the 2D filter size. Bigger filters may increase the maximum possible correlation. The correlation threshold may also depend on the expected noise levels of images of that device model. More noise may lower the maximum possible correlation. For each device model, the correlation thresholds and the number of adjacent positions that must exceed the threshold may be determined empirically.

The size of the 2D filters may be configured per device model, due to variations of the length and width of the segments 522 with respect to the size of the segmented display panel 102 for different models of the external device 106. Referring to FIGS. 17B 17A and 17B, as with display panel edge detection, the 2D filters may be structured to mimic the shape of the LCD segments, minus the overlap at the end of each segment between that segment and its neighbors. Thus, the 2D filters do not have to be square.

The search for segments 522 may yield a list of segments that are detected in an individual digit box 518. This list may be mapped to an output character 524, using a known representation of that character 524 on a segmented display 102. The software application 118 may support only numeric information. The software application 118 may also support alphanumeric information that could be interpreted from the segmented display 102. Some segmented displays, such as seven-segment displays 104, have a very limited set of alphanumeric characters that can be represented. For example, in seven-segment displays 104 the alphabetical characters "H" and "L" are often used along with a zero and one to display "HI" and "LO" values, with the "H" shown as a rotated-to-upside-down 4.

The mapping of detected segments 522 to output characters 524 is not necessarily one-to-one. The image processing subsystem may map partial matches into relevant output characters. For example, in a seven-segment display the digit 3 with the bottom flat segment missing may still be treated as a 3, and a 7 with the lower right vertical segment missing may still be treated as a 7. The partial matches may be specific to each model of the external device 106, as the common errors may vary according to the layout of the display 102.

For example, suppose an external device 102 with a seven-segment display 104 can only output a maximum numeric value of 5 in its leftmost digit. The image processing subsystem finds the segments 522 of the seven-segment digit 6 in the digit box 518 for the leftmost character. The image processing subsystem 400 may interpret the segments 522 as a 5 with an extra lower left vertical segment and determine the digit box 518 contains a 5.

Referring to FIG. 17B, the image processing subsystem 400 may independently examine each digit box 518 for a character 524.

Referring to FIG. 7, the twelfth step 426 in image processing may be combining the individual characters 524 into net OCR output. The net OCR output from each of the individual characters 524 in the external segmented display 102 may be combined by the image processing subsystem 400 into an OCR result string 528 that is a candidate for becoming the output of the reading session 302.

For example, the OCR result string 528 for a typical glucose meter reading might typically be "150," the combination of the output of three individual character detection fields in a given order. The order in which the individual detection field output is combined into a result string, including any spaces or other special characters, may be defined in the software application 118 as a set of configuration parameters 116, on a per-device-model basis. However, the fundamental approach is ordinarily very similar across all models of the external device 106 in a given type. For example, in general all glucose meters have a three-digit display.

In an embodiment, the individual character 524 results are combined into the OCR result string 528 consisting of characters from the image, with a "#" character separating individual fields displayed on the device 106. For example, an image of a blood pressure meter that was reading systolic 140, diastolic 80, and heart rate 63 would result in a result string of "140#80#63" when correctly read. In a further embodiment where the image processing subsystem 400 can only read numerals, the result string 528 consists only of numerals and the "#" character.

Referring to FIG. 7, the thirteenth step 428 in image processing may be validating the candidate result string 528. A number of heuristics may be used by the image processing subsystem 400 for this purpose. Configuration parameters 116 for the particular device model may determine which heuristics are used. The validation heuristic selection configurations for each device model may be determined empirically.

The simplest heuristic, which may be used for all devices, is a check for whether the result 528 has the minimum number of numeric digits for each separate number of the segmented display 102. For each model of the external device 106, configuration parameters 116 may indicate the minimum digit counts for each number. For example, the image processing subsystem 400 may check a glucose meter's value for at least two numeric digits or the alphabetic characters "LO" or "HI." Conventionally, valid blood glucose readings are always greater than 99 when not exceeding the measurement range of the device.

Another heuristic which may be used for all devices is a valid character values check. For each model of the external device 106, configuration parameters 116 may indicate the valid values for each character 524. For example, the image processing subsystem 400 may check whether the first digit of a glucose meter is blank, 1, 2, 3, 4, 5, L, or H, the only valid values in that digit box 518 for that model of glucose meter.

The validation may be repeated after each of the subsequent image processing steps. The validity of the current result may determine which subsequent operations are performed.

Figure 18A:
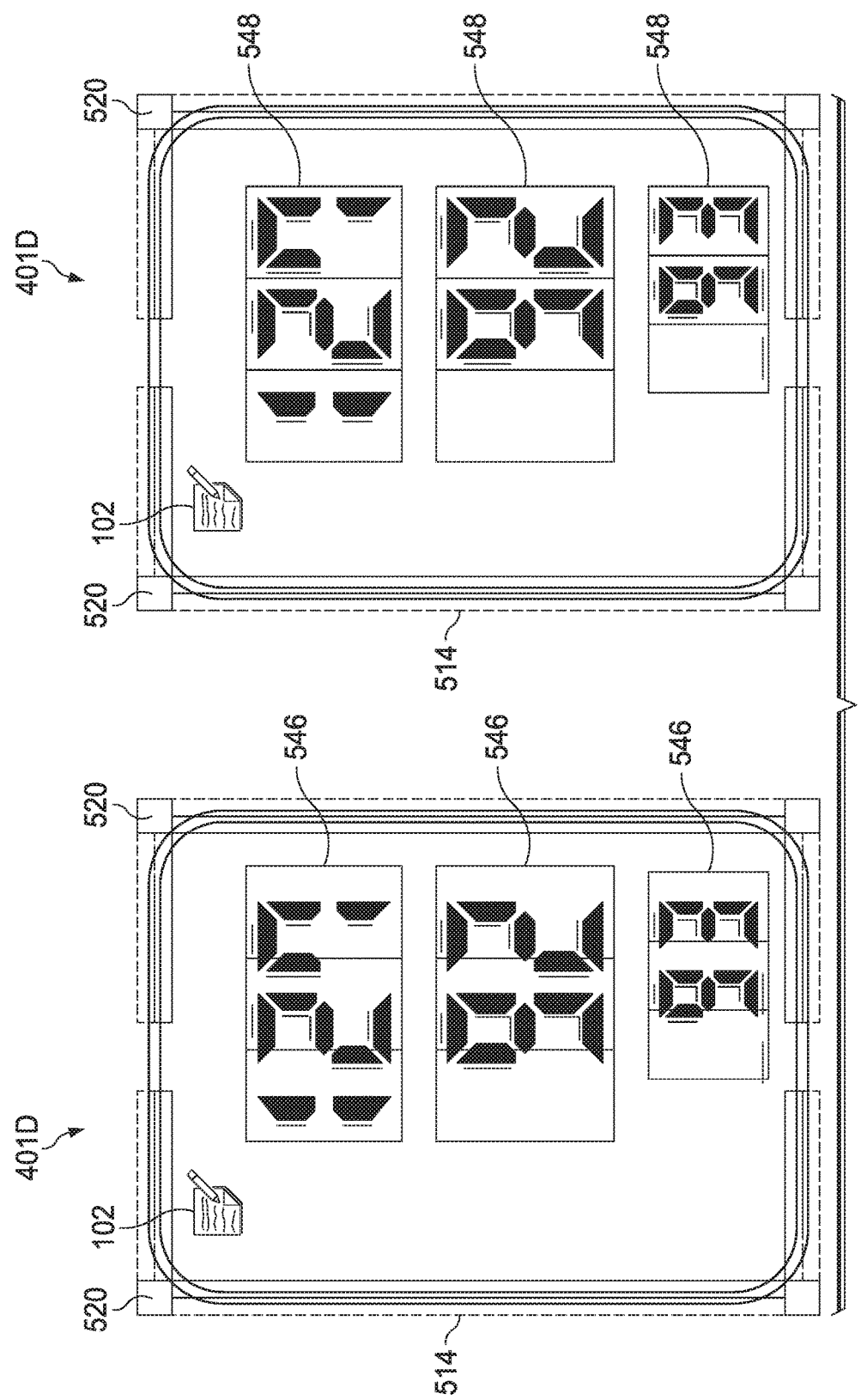
FIGS. 18A and 18B depict exemplary X dimension shifting and resizing operations.

Referring to FIGS. 7 and 18A the fourteenth step 430 in image processing may be shifting the digit boxes 518. Once an initial pass has been made to read the character 524 in each digit box 518, the location of one or more putative display segments may be known, having been found during the search for display segments 522 in each digit box 518. These previously found segments may be used to make adjustments to the area in which the image processing subsystem 400 searches for characters 524.

For each vertical segment 522 found in the external device display 102, the location found for that segment 522 may be compared to the expected location for the segment 522. The difference in the locations may be called the per-segment error for that segment 522. The average per-segment error for vertical segments 522 may then be used as an estimate for the left-to-right shift of the digit boxes 518.

Similarly, for each horizontal segment 522 found in the external device display 102, the location found for that segment 522 may be compared to the expected location for the segment 522. The difference in locations may be called the per-segment error for that segment 522. The average per-segment error for horizontal segments 522 may then be used as an estimate for the top-to-bottom shift of the digit boxes 518.

All of the digit boxes 518 may be shifted by the same amount, because each individual digit box 518 may not contain enough information to calculate a statistically useful estimate of the shift of that digit box 518 alone. For example, a digit box 518 containing the numeral "1" in a conventional seven-segment display would only have two segments 522. Additionally, the primary source of error in the location of the digit boxes 518 is often the initial determination of the display panel edges. This determination may affect all of the digit boxes 518 equally since they may be initially positioned with respect to the display panel edges. FIG. 18A shows a shift of all the digit boxes 518 along the X dimension from a first position 546 to a second position 548. The shift of the digit boxes 518 may be performed on the same size digit boxes 518, or on all the digit boxes 518 as shown in FIG. 18A.

The individual digit boxes 518 may then be adjusted according to the estimated shifts in two dimensions, and the image processing subsystem 400 may make a new attempt to read the characters 524 in the shifted digit boxes 518. The image processing subsystem 400 may then determine if the resulting OCR result 528 is valid as determined by the validation step.

If the OCR result 528 after making the shift is valid and the OCR result 528 before making the shift was not valid, then the image processing subsystem 400 may retain the shifted result 528. However, even if the output before making the shift was not valid, the image processing subsystem 400 may use "result comparison heuristics" to determine if the post-shift result is worse.

Referring to FIG. 7, the fifteenth step 432 in image processing may be determining if the shift has improved the OCR result string 528. Result comparison heuristics may be used to judge whether a new OCR result 528 has lost ground with respect to the previous OCR result 528, and therefore whether the latest operation should be undone. A number of result comparison heuristics are possible. Which heuristics are applied and the priority of application of the relevant heuristics may be determined by configuration parameters 116 for the external device 106.

Note that, logically, OCR result 528 comparisons cannot be done on the basis of which OCR result 528 is more correct in the absolute sense. The image processing subsystem 400 is in the process of determining the correct OCR result, and it therefore cannot determine which of two OCR results 528 is more correct. Instead, the result comparison heuristics may assess the quantitative metrics that are available. The image processing subsystem 400 may assume that each subsequent operation increases the accuracy of the OCR result, and so each operation's new result should be retained unless a result comparison heuristic indicates the new OCR result 528 is sufficiently worse than the previous OCR result 528 according to some quantitative metric. If the result is sufficiently worse, the operation in question may be rolled back (undone).

One possible heuristic for result comparisons is the average error of individual external display segments. This is the same quantity that may be used to estimate the required left-right and up-down shifts in the shifting of the digit boxes. If the average error is greater after an operation, the operation may be rolled back, although this may depend on the device model being read.

Note that the average error is not guaranteed to be a good heuristic for all situations, as an operation such as a shift may bring many more display segments into consideration, and may result in greater average error, even though there are more valid digits present, making the net result better overall. The average error heuristic may only be suitable for a small number of device models.

Another possible heuristic for result comparisons is the number of display segments 522 found. An OCR result 528 that has less than half of the display segments 522 than another OCR result 528 may be judged to be inferior by this heuristic. However, minor differences in the display segment 522 count may be ignored. It is entirely possible for a more accurate result to have fewer segments. For example, digit boxes 518 may be shifted away from an area containing noise but no characters, and onto an area containing characters but no noise. This heuristic may be suitable for most device models.

Yet another possible heuristic for result comparisons is the number of valid individual characters 524 in the result. A result that has fewer valid individual characters 524 may be judged to be inferior according to this heuristic. For example, if the result after an operation is "137" and the result before the operation is "37", the operation may be retained (not rolled back). This heuristic may be suitable for most device models.

Figure 18B:
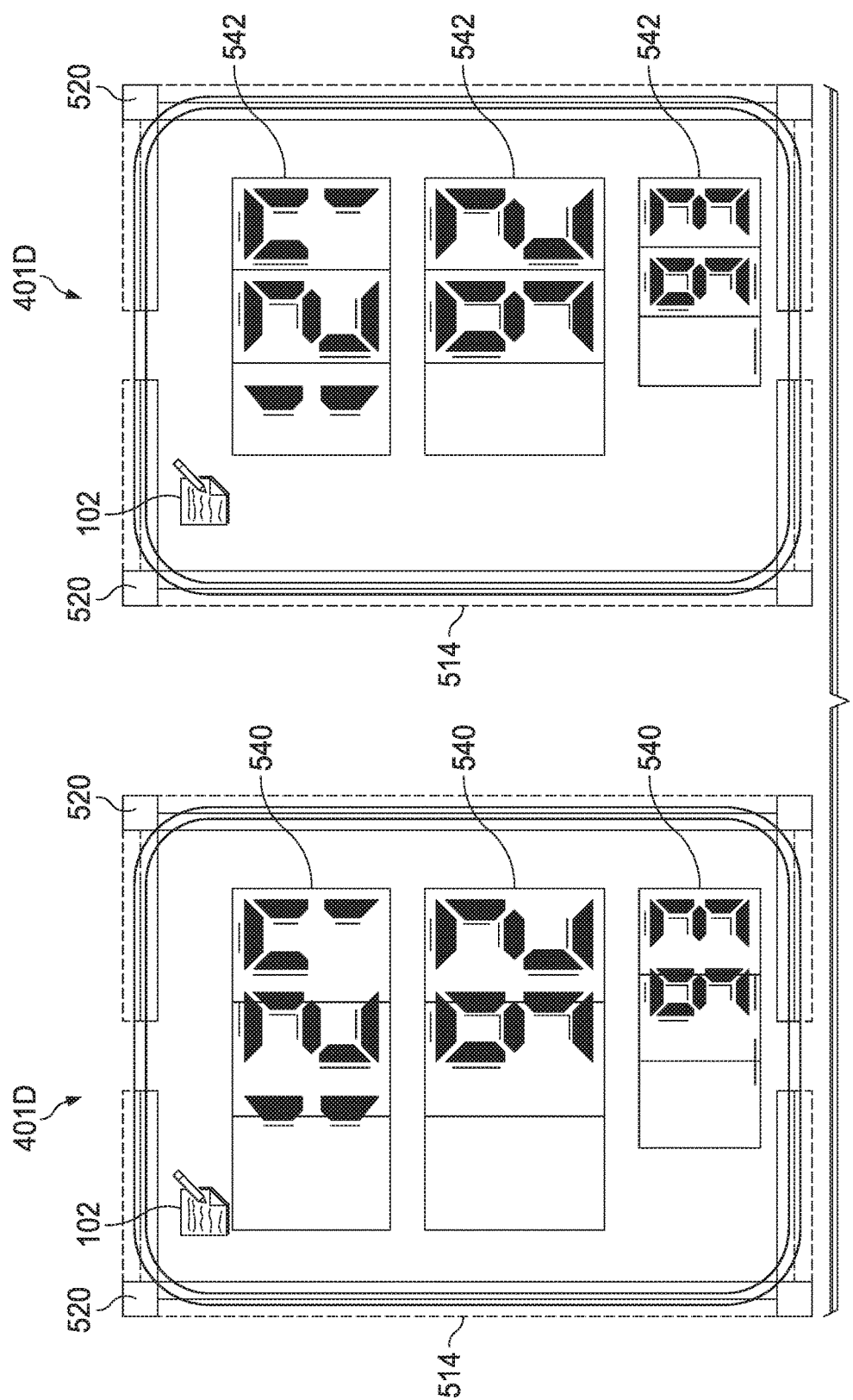

Referring to FIGS. 7 and 18B, the sixteenth step 434 in image processing may be resizing the digit boxes 518. Following the shifting of the digit boxes 518 (and, depending on the result comparison, possibly rolling back the shifting), the digit boxes 518 may be resized. Two possible resizing methods may be used to resize the digit boxes.

Linear regression is a first possible resizing method. FIG. 18B shows a resizing of the digit boxes 518 along the X dimension via regression from a first size 540 to a second size 542. The resizing of the digit boxes 518 may be performed on the same size digit boxes 518, or on all the digit boxes 518 as shown in FIG. 18B. The regression may be performed for the relationship between the position of a segment and the error (with respect to the segment's expected position) of that segment. The idea is that if the individual character bounds are the correct size in a given dimension, the error should not vary systematically along that dimension. The image processing subsystem 400 may perform linear regression to generate an estimate of the increase in error with increasing distance along a given axis.

For the horizontal axis, the rate of increase of error along the horizontal axis may be multiplied by the current width of an individual digit box 518 to generate an error estimate for that width. The error estimate may then be applied to correct the individual digit box bound width. Similarly, the rate of increase of error along the vertical axis may be used to control the digit box bound height.

Linear regression is a powerful technique for situations where the pre-existing bounds are roughly correct, but linear regression can produce poor results when parts of one actual digit are split up among estimated digit boxes (leading to a failure of the assumption of continuously increasing or decreasing error).

Figure 20:
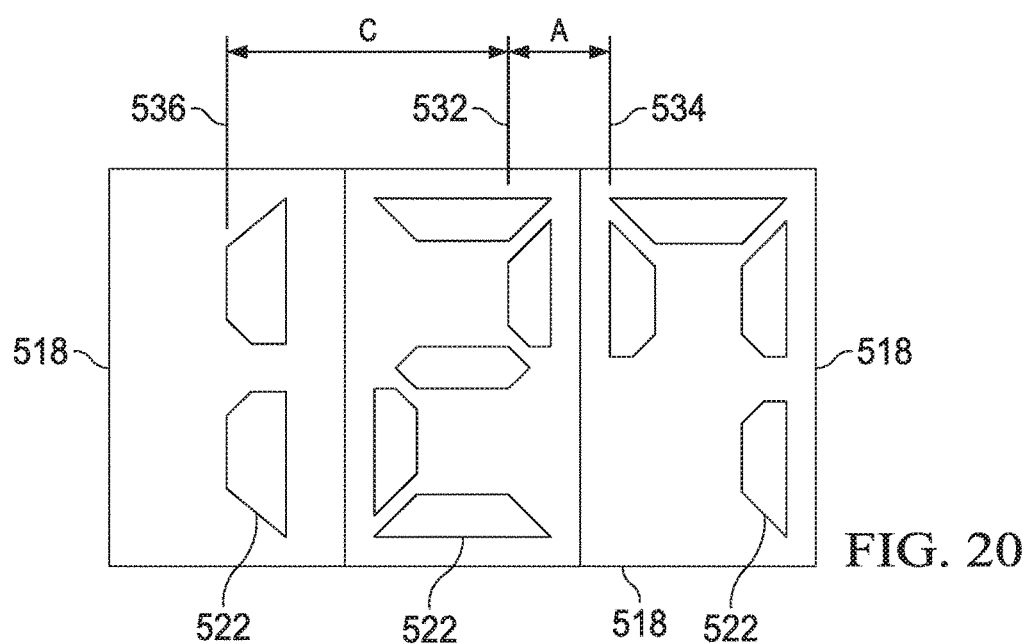
FIG. 20 depicts an exemplary segment gap ratio assessment.

Referring to FIG. 20, segment trio gap comparison is a second possible digit box resizing 434 method. In contrast to linear regression, which may consider all display panel segments 522, the segment trio gap comparison may use only three segments 522 to estimate the correct size of each digit box 518. In segment trio gap comparison, a vertical segment may be chosen as the primary segment 532. The vertical segment may be chosen from among the vertical segments of the middle digit for displays with an odd number of digits, or from the digit to the right of center for displays with an even number of digits. The primary vertical segment 532 may be compared to its left 536 and right 534 neighbor vertical segments, to compute the primary-to-left distance C versus the primary-to-right distance A as a right-to-left distance ratio. The right-to-left distance ratio should be constant for a given set of three display segments 522 in a given relationship. There are a limited number of possible relationships in a real number for vertical segments 522. For example, there is the situation where the primary vertical segment 532 is the right side of a digit, the left neighbor segment 536 is the left side of that same digit, and the right neighbor segment 534 is the left side of the next digit over to the right.

The relative distances between segments in an "ideal" image, an image where the segments 522 appear in exactly their expected positions, may be called the "ideal ratios" for the segments. In other words, the ideal ratios are the distances between the expected segment positions. The ideal ratios may be defined exactly for a given device model. For device models using the same standard displays, e.g. standard seven-segment display 104, the ideal ratios may also be the same between device models. The ideal ratios for each device model may be in the configuration parameters 116 for that device model.

The ideal ratios may be based on four distances, which for discussion will be labelled A through D in order of typical relative length. Distance A is the distance from the upper right segment 522 of a digit box 518 to the upper left segment 522 of the neighboring digit box 518 to the right. Distance B is the distance from the upper right segment 522 of a digit box 518 to the upper left segment 522 of that same digit box 518. Distance C is the distance from the upper right segment 522 of a digit box 518 to the upper right segment 522 of the neighboring digit box 518 to the right. Distance D is the distance from the upper right segment 518 of a digit box 522 to the upper left segment of the neighboring digit box 518 to the left.

Conventionally, every numeric digit has at least one upper and one lower vertical segment. Therefore, in an image where no segment is ruined by noise or glare, detected segment-to-segment distances traced without interruption (that is, from one segment to the nearest neighboring segment on one side or the other) can be expected to fit one of these four distances. To perform the resizing correction, the image processing subsystem 400 may assess the distance from the primary segment 532 to its nearest neighbor on the right, and to its nearest neighbor on the left. The "distance ratio" may be expressed as the distance on the right divided by the distance on the left. That ratio may then be compared to a list of all the ideal ratios of the four distances: A/B, B/A, A/C, C/A, A/D, D/A, B/C, C/B, B/D, D/B, C/D, and D/C. The image processing subsystem 400 may choose the ideal ratio which is the most similar to the computed ratio. The image processing subsystem 400 may then adjust the digit box 518 so that the three segments 522 are positioned in their respective ideal locations in their respective digit boxes 518.

For example, suppose the best matching ideal ratio is A/B. The image processing subsystem 400 may make adjustments to the widths of the digit box 518 in order to match up the expected segment positions in each digit box 518 to the actual segment positions and ratios observed. The primary segment 532 may be positioned as the upper right segment 522 in its digit box 518. The segment 522 to the right of the primary segment 532 may be positioned as the upper left segment 522 in the neighboring digit box 518 to the right of the primary segment 32. The segment 522 to the left of the primary segment 532 may be positioned as the upper left segment 522 in the digit box 518 of the primary segment 532.

A similar procedure may be done for horizontal segments, though there is only one possible trio for horizontal segments in a single line display. If there are insufficient segments 522 detected to form a trio in the vertical or horizontal dimension, or if no ideal left-to-right ratio is within a set tolerance of the computed left-to-right ratio, then the image processing subsystem 400 may avoid using this trio gap comparison approach to resize digit boxes.

Both resizing methods may be unsuitable for single digit displays in the horizontal dimension, as such displays may have a maximum of only two vertical segments along the same horizontal line. Two vertical segments may be too few for linear regression and too few to form a trio for segment trio gap comparison. The image processing subsystem 400 may not resize the digit boxes 518 if the segmented display 102 is a single digit display in the horizontal dimension.

Referring to FIG. 7, the seventeenth step in image processing subsystem 400 may be determining if resizing the digit boxes 518 has improved the OCR result string 528. This step may be performed using result comparison heuristics, in the same manner as determining if the shift has improved the OCR result 528. If resizing the digit boxes 518 produces a significantly worse result, the resizing may be rolled back.

The shifting of digit boxes 518 and resizing of digit boxes 518 may be repeated or performed in a different sequence. For example, the optimal combination for some device models may be to shift digit boxes 518 horizontally, resize digit boxes 518 horizontally, shift digit boxes 518 vertically, resize digit boxes 518 vertically, shift digit boxes 518 horizontally a second time, and then resize digit boxes 518 vertically a second time. The optimal sequence of shifting and resizing may be determined empirically for each device model. Typically, device models with more variation in the detection of the horizontal panel edge positions will require more correction steps for the vertical position of the digit boxes, and so on.

Referring to FIG. 7, the eighteenth step in image processing may be swapping characters 524 for more-likely characters. When the character 524 read for a digit box 518 is determined to be impossible for a given position in a given device model, the image processing subsystem 400 may consult a list of the most likely substitutes for that position given the device model, the position, and the detected erroneous character. Each digit box 518 of a device model may have a separate list. The lists may be part of the configuration parameters 116 for the device model. The image processing subsystem 400 may replace the detected erroneous character with the substitute.

For example, when the image processing subsystem 400 detects a "9" in the first three digits in a glucose meter display, the image processing system 400 may recognize (due to validation as previously discussed) that the "9" is not valid. The image processing subsystem 400 may consult a table to determine "3" is the correct substitute (a "9" without an extra erroneous left upper vertical segment.) The image processing subsystem 400 may then replace the "9" with a "3."

Referring to FIG. 7, after swapping characters 524 for more-likely characters, the image processing subsystem 400 may then report the OCR result 528 to the software application. The reported OCR result 528 may be the OCR partial result 208 for use by the software application 118 in determining the OCR final result string 216, as discussed above.

As an example of an alternative architecture, the reading device 108 may send images to a remote device which performs the functions of the image processing subsystem 400. As other examples, the reading device 108 could be a desktop computer, laptop computer, tablets, PDAs, and the like. As further examples, instead of OCR of characters, image matching on the entire image or image matching of individual characters could be used.

It is noted that the embodiments disclosed are illustrative rather than limiting in nature and that a wide range of variations, modifications, changes, and substitutions are contemplated in the foregoing disclosure and, in some instances, some features may be employed without a corresponding use of the other features. Many such variations and modifications may be considered desirable by those skilled in the art based upon a review of the foregoing description of various embodiments.

We claim:

1. A method for optical reading of a segmented display using a reading device, the method comprising:
   a camera viewing the segmented display and displaying a real time image of the segmented display on a video screen of the reading device, the camera connected to the reading device;
   the segmented display being part of an external segmented display device, the segmented display comprising a number of character segments configured to be selectively activated to collectively display a plurality of alphanumeric characters, the activated and displayed character segments each forming at least a portion of at least one of the plurality of characters and having a length, position and orientation on at least one of the alphanumeric characters specific to the segmented display;
   the reading device comprising a data reading application and one or more configuration parameters specific to the external segmented display device being read, and the data reading application performing a method, comprising:

capturing and storing one or more still captured images from the viewing of the segmented display;

while the camera is viewing and displaying the real time image of the segmented display on the video screen, the reading device generating one or more partial optical character recognition (OCR) result readings of at least a portion of an alphanumeric character formed by the activated character segments of the external segmented display device for each of the one or more still captured images of the segmented display, the generating comprising processing each of the one or more still captured images using the one or more configuration parameters specific to the external segmented display device being read and recognizing one or more character segments of the segmented display;

based at least in part on the generated one or more partial OCR result readings, the reading device providing one or more real time feedback cues on the reading device, wherein the one or more real time feedback cues comprise the reading device displaying, along with the real time image of the segmented display, an alphanumeric value indicating the generated one or more partial OCR result readings of the segmented display; and the reading device determining a final OCR result reading of the segmented display using the one or more partial OCR result readings generated from the one or more stored still captured images of the segmented display.

2. The method in claim 1, wherein, in addition to the reading device displaying an alphanumeric value indicating the generated one or more partial OCR result readings of the segmented display, the method performed by the data reading application further comprises:

based at least in part on the generated one or more partial OCR result readings, if the reading device determines one or more still captured images of the segmented display can be improved by adjustments of the camera or the segmented display, at least one of the one or more real time feedback cues provided on the reading device prompting the adjustments of the camera or the segmented display; and continuing to capture and store the one or more still images of the segmented display from the viewing of the segmented display while the one or more real time feedback cues are being provided on the reading device.

3. The method in claim 2, wherein the at least one of the one or more real time feedback cues prompts a user to focus the camera.

4. The method in claim 2, wherein the at least one of the one or more real time feedback cues prompts a user to adjust the camera angle to straighten the view of the segmented display.

5. The method in claim 2, wherein the adjustment of the camera comprises at least one of focusing the camera, changing a camera angle, tilting the camera, panning the camera, and changing a camera zoom.

6. The method in claim 2, wherein the adjustment of the segmented display comprises tilting, rotating, and changing the lighting conditions on the segmented display.

7. The method in claim 2, wherein the at least one of the one or more real time feedback cues prompts a user to move the camera closer or farther away from the segmented display.

8. The method in claim 2, wherein the at least one of the one or more real time feedback cues prompts a user to adjust the lighting conditions on the segmented display.

9. The method in claim 2, wherein the at least one of the one or more real time feedback cues comprises showing a user a feedback instructional message instructing the user how to use a previous real time feedback cue.

10. The method in claim 2, further comprising adjusting a duration of the at least one of the one or more real time feedback cues shown on the reading device, the adjusted duration determined using a timeliness of a previous response by a user to a previous real time feedback cue.

11. The method in claim 2, wherein a magnitude of a condition required to prompt the at least one of one or more real time feedback cues on the reading device is adjusted based on a user's consistency in correctly responding to a previous real time feedback cue.

12. The method in claim 1, wherein the processing of each of the one or more still captured images of the segmented display further comprises:

determining a location for one or more digit boxes on the still captured image of the segmented display, wherein the one or more digit boxes are each estimated to contain a character formed by the activated character segments;

detecting the activated character segments in each of the one or more digit boxes;

examining the activated character segments detected in each of the one or more digit boxes to read an output character for each of the one or more digit boxes; and combining the output characters of each of the one or more digit boxes into a partial OCR result reading.

13. The method in claim 12, wherein the examining of the one or more independent segments in each of the one or more digit boxes further comprises:

reading the output character for a digit box, the reading of the output character comprising mapping the detected character segments in the matching digit box to a representation of the output character; and reading a partially output character for a partially matching digit box, the reading of the relevant output character comprising mapping the independent segments detected in the partially matching digit box to a representation of the partially matching output characters, the mapping using the one or more configuration parameters.

14. The method in claim 12, further comprising validating the partial OCR result reading using the one or more configuration parameters.

15. The method in claim 14, wherein validating the partial OCR result reading further comprises checking for whether the partial OCR result reading has a minimum number of digits, the minimum number of digits for the partial OCR result reading determined using the one or more configuration parameters.

16. The method in claim 14, wherein validating the partial OCR result reading further comprises determining whether each of the output characters in the partial OCR result reading is valid, the determining of whether the output character is valid comprising using the one or more configuration parameters.

17. The method in claim 12, further comprising shifting or resizing the one or more digit boxes using the one or more independent segments already detected.

18. The method in claim 12, wherein reading the output character for each of the one or more digit boxes further comprises:
   determining whether the output character read for each of the one or more digit boxes is impossible using the one or more configuration parameters; and
   if the output character read for any of the one or more digit boxes is determined to be impossible, swapping the impossible character with a more-likely substitute character, the more-likely substitute character determined using the one or more configuration parameters.

19. The method in claim 1, further comprising validating the final OCR result reading using the one or more configuration parameters.

20. The method in claim 19, wherein validating the final OCR result reading further comprises checking for whether the partial OCR result reading has a minimum number of digits, the minimum number of digits for the partial OCR result reading determined using the one or more configuration parameters.

21. The method in claim 19, wherein validating the final OCR result reading further comprises determining whether each of the output character in the final OCR result reading is valid, the determining of whether the output character is valid comprising using the one or more configuration parameters.

22. The method in claim 1, further comprising displaying health measurement data on the segmented display.

23. The method in claim 1, further comprising indicating on the reading device the type of device the external segmented display device is.

24. The method in claim 1, wherein the external segmented display device is a health monitoring device.

25. The method in claim 1, wherein the processing of the one or more still images further comprises cropping, decimating, and local adaptive thresholding the one or more still images.

26. The method in claim 1, further comprising prompting a user whether to accept the final OCR result reading.

27. The method in claim 1, wherein the segmented display is one of a seven-segment display, a fourteen-segment display, or a sixteen-segment display.

28. The method in claim 1, further comprising providing a smartphone or tablet comprising the camera, the reading device, and the video screen.

29. The method in claim 1, further comprising:
   determining if a set number of the most recent partial OCR result readings match; and
   using the matching partial OCR result reading as the final OCR result reading if the set number of the most recent partial OCR result readings match.

30. The method in claim 1, further comprising prompting a user with a survey question to associate meta-data with the final OCR result reading.

31. The method of claim 1, wherein the alphanumeric value displayed indicates the most recently generated one or more partial OCR result readings of the segmented display.

32. The method of claim 1, further comprising the reading device displaying along with the real time image of the segmented display, an alphanumeric value indicating the final OCR result reading of the segmented display.

33. A method for optical reading of one or more alphabetic or numeric characters on an external electronic display using a reading device, the method comprising:
   a camera viewing the external electronic display and displaying a real time image of the external electronic display on a video screen of the reading device, the camera connected to the reading device, wherein the real time image displayed by the camera comprises one or more alphabetic or numeric characters appearing on the external electronic display;
   the reading device performing a method, comprising:
      capturing and storing a plurality of still captured images from the viewing of the external electronic display, the plurality of still captured images comprising a first still captured image and a second still captured image, wherein the second still captured image is more recent than the first captured still image;
      while the camera is viewing and displaying on the video screen the real time image of the external electronic display, the reading device generating a partial optical character recognition (OCR) result reading for each of the first and second still captured images of the external electronic display, wherein each of the result readings comprises one or more alphabetic or numeric characters corresponding to one or more characters of the external electronic display viewed by the camera; and
      while the real time image of the external electronic display is displayed on the video screen, the reading device displaying on the video screen the partial OCR result reading for the first still captured image and subsequently displaying the partial OCR result reading for the more recent second still captured image, thereby allowing comparison of the real time image of the external electronic display with the plurality of partial OCR readings.

34. The method of claim 33, further comprising providing a smartphone or tablet comprising the camera, the reading device, and the video screen.

35. The method of claim 33, wherein the method performed by the reading device further comprises:
   determining if a given proportion of the plurality of the most recent partial OCR result readings match; and
   if the given proportion of the most recent partial OCR result readings match, selecting the matching partial OCR result reading as the final OCR result reading.

36. The method of claim 35, further comprising providing a smartphone or tablet comprising the camera, the reading device, and the video screen.

37. The method of claim 33, further comprising:
   providing a smartphone or tablet comprising the camera, the reading device, and the video screen;
   determining if a set number of the most recent plurality of partial OCR result readings match; and
   using the matching partial OCR result reading as the final OCR result reading if the set number of the most recent partial OCR result readings match.

38. A method for optical reading of an alphabetic or numeric characters on an external electronic display using a reading device, the method comprising:
   a camera viewing the external electronic display and displaying a real time image of the external electronic display on a video screen of the reading device, the camera connected to the reading device, wherein the real time image displayed by the camera comprises one or more alphabetic or numeric characters appearing on the external electronic display;
   the reading device performing a method, comprising:

capturing and storing a plurality of still captured images from the viewing of the external electronic display, the plurality of still captured images comprising a first still captured image and a second still captured image, wherein the second still captured image is more recent than the first captured still image;

while the camera is viewing and displaying on the video screen the real time image of the external electronic display, the reading device generating a partial optical character recognition (OCR) result reading for each of the first and second still captured images of the external electronic display, wherein each of the result readings comprises one or more alphabetic or numeric characters corresponding to one or more characters of the external electronic display viewed by the camera;

determining if a given proportion of the plurality of the most recent partial OCR result readings match; and if the given proportion of the most recent partial OCR result readings match, selecting the matching partial OCR result reading as the final OCR result reading; and while the real time image of the external electronic display is displayed on the video screen, the reading device displaying on the video screen the final OCR result reading.

39. The method of claim 38, further comprising:
providing a smartphone or tablet comprising the camera, the reading device, and the video screen;
determining if a set number of the most recent plurality of partial OCR result readings match; and
using the matching partial OCR result reading as the final OCR result reading if the set number of the most recent partial OCR result readings match.

40. The method of claim 38, further comprising providing a smartphone or tablet comprising the camera, the reading device, and the video screen.

\* \* \* \* \*